United States Patent
Brogden

(12) 
(10) Patent No.: US 9,218,940 B1
(45) Date of Patent: Dec. 22, 2015

(54) METHOD AND APPARATUS FOR SLICE AND VIEW SAMPLE IMAGING

(71) Applicant: FEI Company, Hillsboro, OR (US)

(72) Inventor: Valerie Brogden, Portland, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/292,606

(22) Filed: May 30, 2014

(51) Int. Cl.
*H01J 37/305* (2006.01)
*H01J 37/26* (2006.01)

(52) U.S. Cl.
CPC ............. *H01J 37/3056* (2013.01); *H01J 37/26* (2013.01); *H01J 2237/31749* (2013.01)

(58) Field of Classification Search
USPC ......................................... 250/306, 307, 310
See application file for complete search history.

(56) References Cited

U.S. PATENT DOCUMENTS

| | | | |
|---|---|---|---|
| 5,435,850 A | 7/1995 | Rasmussen | |
| 5,851,413 A | 12/1998 | Casella et al. | |
| 7,348,556 B2 | 3/2008 | Chitturi et al. | |
| 7,423,266 B2 * | 9/2008 | Tashiro et al. | 250/310 |
| 7,858,936 B2 | 12/2010 | Bray et al. | |
| 7,977,631 B2 | 7/2011 | Mulders et al. | |
| 8,350,237 B2 | 1/2013 | Tanner | |
| 2006/0226376 A1 * | 10/2006 | Fujii | 250/492.21 |
| 2009/0283677 A1 * | 11/2009 | Ikku | 250/307 |
| 2010/0033560 A1 | 2/2010 | Kawasaki et al. | |
| 2010/0054565 A1 | 3/2010 | Quinto et al. | |
| 2010/0301211 A1 | 12/2010 | Miller | |
| 2013/0320209 A1 | 12/2013 | Shichi et al. | |

* cited by examiner

*Primary Examiner* — Kiet T Nguyen
(74) *Attorney, Agent, or Firm* — Scheinberg & Associates, PC; Michael O. Scheinberg; John E. Hillert

(57) ABSTRACT

Methods, apparatuses, and systems for slice and view processing of samples with dual beam systems. The slice and view processing includes exposing a vertical wall of a trench formed in a sample surface; capturing a first image of the wall by interrogating the wall with an interrogating beam while the wall is at a first orientation relative to the beam; capturing a second image of the wall by interrogating the wall with the beam while the wall is at a second orientation relative to the beam, wherein first distances in the first image between a reference point and surface points on the wall are different than second distances in the second image between the reference point and the surface points; determining elevations of the surface points using the first distances and the second distances; and fitting a curve to topography of the wall using the elevations.

25 Claims, 16 Drawing Sheets

METHOD AND APPARATUS FOR SLICE AND VIEW SAMPLE IMAGING

TECHNICAL FIELD

The present invention relates to methods, apparatuses, and systems for imaging samples in two and three dimensions using beams, such as charged particle beams.

BACKGROUND

Electron microscopy offers the opportunity to investigate the ultrastructure of a wide range of biological and inorganic specimens in 3-D at high resolution. In the field of biological sciences, for example, electron microscopy allows the observation of molecular mechanisms of diseases, the conformation of flexible protein structures and the behavior of individual viruses and proteins in their natural biological context. As another example, electron microscopy plays an important quality control function in the manufacture of semiconductors and electronic devices by allowing for the detection and characterization of nanoscale defects in electrical, optical, and micromechanical systems, which may affect the performance of such products. Defects can include contaminant particles that become embedded in a product during fabrication or a manufacturing defect, such as a bridge creating a short circuit between two closely spaced conductors that are intended to be electrically separated from each other. One technique employed with electron microscopy to carry out such investigations is called Slice-and-View™ (hereafter "slice and view"). This technique is typically performed with a dual beam system, that is, a system combining a focused ion beam (FIB) device and a scanning electron microscope (SEM) such as the DualBeam® instruments commercially available from FEI Company, the assignee of the present invention.

In the slice and view technique, as illustrated by FIG. 1, the focused ion beam cuts and slices a sample with high precision to reveal its 3D internal structures or features. Typically, the focused ion beam cuts exposes a cross section, or face, perpendicular to the top of the surface of the sample material having the hidden feature to be viewed. Because the SEM beam axis is typically at an acute angle relative to the focused ion beam cuts axis, a portion of the sample in front of the face is preferably removed so that the SEM beam can have access to image the face. After obtaining an image of the face by the SEM, another layer of substrate at the face may be removed using the focused ion beam cuts, revealing a new, deeper face and thus a deeper cross-section of the feature. Since only the portion of the feature at the very surface of the face is visible to the SEM, sequential repetition of cutting and imaging, or slicing and viewing, provides the data needed to reconstruct the sliced sample into a 3D representation of the feature. The 3D structure is then used to analyze the feature.

During slicing, variations in the topography of the surface exposed may occur as the focused ion beam traverses a sample. In some circumstances, the exposed face may have a surface morphology attributable to a phenomenon known colloquially as the "curtaining" effect, which is schematically illustrated in FIGS. 2A and 2B. When a sample 210 contains heterogeneous structures and/or compositions, the material removal rate of focused ion beam 215 from FIB column 220 may vary locally as focused ion beam 215 carries out a line mill 225 across face 230 in the direction of arrows 240. As a result, the surface of the sample exposed by the focused ion beam has a rippled face, or curtain. Local increases in the material removal rate may form concave curtains, such as curtaining artifacts 245A, 245B, and 245C, which penetrate into the face being exposed. Local decreases in the material removal rate may form convex curtains, such as curtaining artifact 250, which protrude from the face being exposed.

Software algorithms for 3-D reconstruction from slice and view imaging generally assume that surface of each slice imaged by the SEM is flat. Applicant has found that the presence of curtaining and other artifacts create topographical variations mean that the surface is not flat and this lack of flatness manifests as noise (e.g., decreased resolution) in the 3-D representation formed from images of the exposed surfaces. Thus, applicant has discovered that there is a need for methods, apparatuses, and systems that take into account variations in the topography of surfaces interrogated by an SEM during slice and view imaging of a sample, such as topographical variations caused by the curtaining effect, in order to improve the resolution of 3-D representations generated therefrom.

SUMMARY

In some embodiments of the disclosure, a method of processing a sample by slice and view processing with a dual beam system is provided that includes: exposing a vertical wall of a trench formed in a surface of a sample by removing a first slice of material from the sample using an etching beam; capturing a first image of the vertical wall by interrogating the vertical wall with an interrogating beam while the vertical wall is at a first orientation relative to the interrogating beam; reorienting the vertical wall relative to the interrogating beam; capturing a second image of the vertical wall by interrogating the vertical wall with the interrogating beam while the vertical wall is at a second orientation relative to the interrogating beam, wherein first distances in the first image between a reference point and surface points on the vertical wall are different than second distances in the second image between the reference point and the surface points; determining elevations of the surface points using the first distances and the second distances; and fitting a curve to a topography of the vertical wall using the elevations.

In some embodiments of the disclosure, an apparatus for observing a feature using dual charged particle beams is provided that includes a focused ion beam column configured to generate, focus, and direct a focused ion beam; an electron beam column configured to generate, focus, and direct an electron beam; one or more processors; and a computer-readable storage medium coupled to at least one of the one or more processors. The computer-readable storage medium includes first executable instructions and second executable instructions. The first executable instructions, when executed, cause the one or more processors to direct the focused ion beam to mill a trench in a surface of a substrate, the trench exposing a vertical wall having an area around a feature to be observed. The second executable instructions, when executed, cause the one or more processors to direct the electron beam to capture a first electron beam image of the vertical wall while the electron beam column is maintained at a first angle of incidence relative to a longitudinal axis of the electron beam column; to change the angle of incidence of between the longitudinal axis and the vertical wall from the first angle of incidence to a second angle of incidence; to direct the electron beam to capture a second electron beam image of the wall while the electron beam column is maintained at the second angle of incidence; and to approximate a topography of the vertical wall based on differences between the first electron beam image and the second electron beam image.

In an embodiment of the apparatus, approximation of the topography of the vertical wall includes calculating three-dimensional coordinates for a plurality of points on the vertical wall using positions of the plurality of points in the first electron beam image and the second electron beam image relative to a reference point in the first electron beam image and the second electron beam image. In an embodiment of the apparatus, approximation of the topography of the vertical wall includes fitting a curve to the three-dimensional coordinates that approximates the topography of the vertical wall. In an embodiment of the apparatus, approximation of the topography of the vertical wall based on differences between the first electron beam image and the second electron beam image includes measuring in the first electron beam image first distances between a plurality of points on the vertical wall and one or more reference points on the vertical wall; and measuring in the second electron beam image second distances between the plurality of points and the one or more reference points.

In an embodiment of the apparatus, the second executable instructions, when executed, cause the one or more processors to change the angle of incidence of between the longitudinal axis and the vertical wall by directing a rotation of a stage. In an embodiment of the apparatus, the second executable instructions, when executed, cause the one or more processors to change the angle of incidence between the longitudinal axis and the vertical wall by directing a repositioning of the electron beam column.

In an embodiment of the apparatus, the apparatus includes third executable instructions that, when executed, cause the one or more processors to direct the focused ion beam to sequentially remove a plurality of slices from a volume of material located behind the vertical wall, wherein the volume of material includes a feature to be observed and sequentially removing the plurality of slices sequentially exposes a plurality of additional vertical walls; and carry out the second executable instructions for each vertical wall of the plurality of additional vertical walls. In an embodiment, the apparatus includes the third executable instructions and fourth executable instructions that, when executed, cause the one or more processors to construct a three-dimensional image of the feature to be observed using the approximations of the topographies of the vertical wall and the plurality of additional vertical walls.

In some embodiments of the disclosure, a particle beam system for slice and view processing a volume of a sample having a feature to be observed is provided. The particle beam system includes an etching beam column configured to emit an etching beam; an interrogating beam column configured to emit an interrogating beam; one or more processors; and a computer-readable storage medium coupled to at least one of the one or more processors. The computer-readable storage medium includes executable instructions that, when executed, cause the one or more processors to direct the etching beam to sequentially remove slices of the sample across a thickness of the volume, the removal of each slice exposing a surface of the sample, and, for each surface exposed: direct the interrogating beam to capture a first image of the surface exposed while maintaining a first angle of incidence between a longitudinal axis of the interrogating beam column and the surface exposed and a second image of the surface exposed while maintaining a second angle of incidence between the longitudinal axis and the surface exposed, and record first positions of pairs of points in the first image and second positions of the pairs of points in the second image, wherein each of the pairs of points includes a point on the surface exposed and a reference point.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present disclosure, and advantages thereof, reference is now made to the following descriptions taken in conjunction with the accompanying drawings, in which.

DETAILED DESCRIPTION

In the following discussion and in the claims, the terms "including" and "comprising" are used in an open-ended fashion, and thus should be interpreted to mean "including, but not limited to . . . . " To the extent that any term is not specially defined in this specification, the intent is that the term is to be given its plain and ordinary meaning. Furthermore, use of the term "and/or" herein shall be construed as an "inclusive" or, and not an "exclusive" or. For example, used herein the phrase "A and/or B" would mean "A, B, or A and B." As another example, used herein the phrase "A, B, and/or C" would mean "A, B, C, or any combination thereof." Further, whenever the terms "automatic," "automated," or similar terms are used herein, those terms will be understood to include manual initiation of the automatic or automated process or step.

As used herein, the terms "mill" and "etch" refer to the removal of material of a sample, and the terms "slice," "slice mill," and "etch a slice" refers to the removal of material from a sample in the shape of a slice. As used herein, the term "slice," when used as a noun, refers to the body of material removed by the FIB to expose a surface. The slice may be characterized, for example by a width dimension, a height dimension, and a thickness dimension, which correspond, respectively, to the edges of the illustrative sample of FIG. 1 aligned with x, y, and z axes shown therein.

An "image," as used herein, means an image displayed on a display unit or on a disposable medium such as paper, as well as a representation thereof in a computer memory, for example. As used herein, the term "image plane" refers to the plane in which an image generated by an interrogating beam system (e.g., a SEM) is formed, whereas the "imaging plane" refers to the cross-section of a sample exposed by removing a slice from the sample using an ablating beam system (e.g., a FIB) device.

The accompanying drawings are intended to aid in understanding various embodiments of the present invention. Unless otherwise indicated, the accompanying drawings are not drawn to scale.

Figure 1:
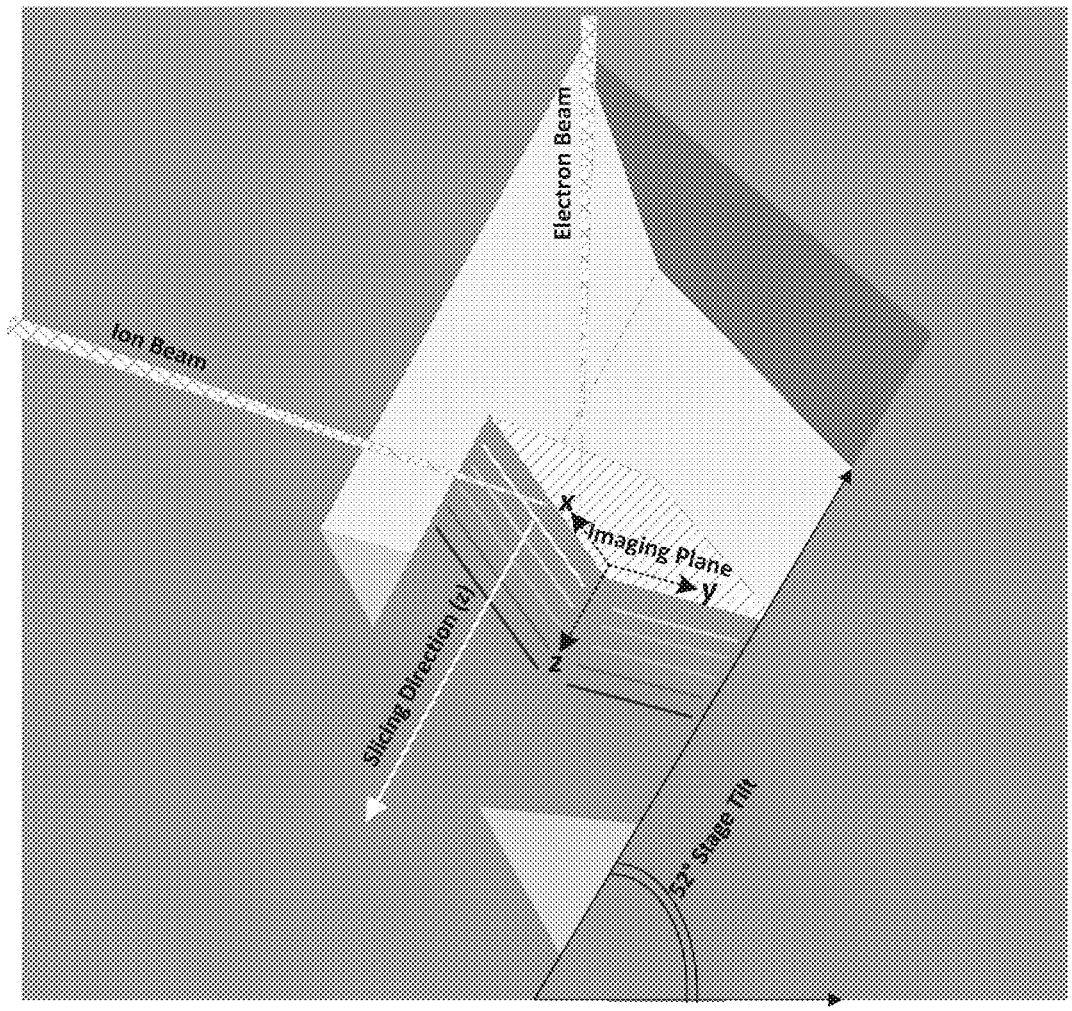
FIG. 1 is a diagram showing slice and view processing of a sample.

Although other coordinate systems may be used to explain and/or implement embodiments of the invention, for simplicity the 3-D coordinate system shown in FIG. 1 is used herein as the coordinate system for the samples and sample environments described in connection with the various illustrative embodiments of the disclosure. Thus, unless indicated otherwise or in different context, the terms "z-axis," "z-coordinate," "z-height," "elevation," "thickness direction," and the like are used herein with reference to the z-axis of FIG. 1; the terms "x-axis", "x-coordinate," "horizontal," "horizontal direction," "horizontal alignment," "width direction," "sample width", "slice width," and the like are used herein with reference to the x-axis of FIG. 1; and the terms "y-axis", "y-coordinate," "vertical," "vertical direction," "vertical alignment," "depth," "height," "height direction," "sample height", "slice height," and the like are used herein with reference to the y-axis of FIG. 1. Accordingly, "height" and "vertical height" will be used synonymously herein to refer to the distance measured from a point to the surface of the sample directly beneath the point along a line parallel to and in the direction of the y-axis of FIG. 1, whereas the "z-height" and "elevation" will be used synonymously herein to refer to the distance from a point to the imaging plane of the sample along an axis parallel to the z-axis of FIG. 1 and intersecting both the point and the imaging plane. Further, as used herein, the depth of a point located in a trench formed in a top surface of the sample (e.g., the surface directly beneath the "slicing direction" arrow of FIG. 1) is measured from a plane overlapping the surface to the point along a line parallel to the y-axis of FIG. 1 and intersecting both the surface of the sample direction of the y-axis of FIG. 1.

In some cases, it may be desirable to provide a method of forming a 3-D representation of a feature by slice and view processing of a sample, wherein the quality (e.g., resolution) of the 3-D representation is improved by characterizing and correcting for topographical variation in the profiles (i.e., deviation from a flat profile) of surfaces imaged on which the 3-D representation is based. In various embodiments, an interrogating beam captures at least two images of each surface of a sample exposed after a slice of material has been removed from the sample by an etching beam. For each surface exposed, the interrogating beam captures a first image of the exposed surface and then captures a second image of the exposed surface after the exposed surface has been reoriented relative to the interrogating beam. In some embodiments, the etching beam is a focused ion beam of a FIB device and the interrogating beam is an electron beam of a SEM. In some embodiments, a sample is mounted on a stage, and the reorientation of the exposed surface relative to the interrogating beam comprises rotating the sample by an angle $\theta$. In some embodiments, the reorientation of the exposed surface relative to the interrogating beam comprises changing an angle of incidence between the interrogating beam and the exposed surface by repositioning a source of the interrogating beam. By imaging each of the surfaces of a sample exposed during slice and view processing from two different perspectives (i.e., capturing the second image while maintaining the exposed surface at an orientation, relative to the interrogating beam, that is different from the orientation maintained while capturing the first image), topographical information about each of the exposed surfaces can be obtained and used to generate a 3-D representation of a feature in the sample having greater resolution than would have been otherwise been achieved had the exposed surfaces been assumed to be flat.

Figure 3:
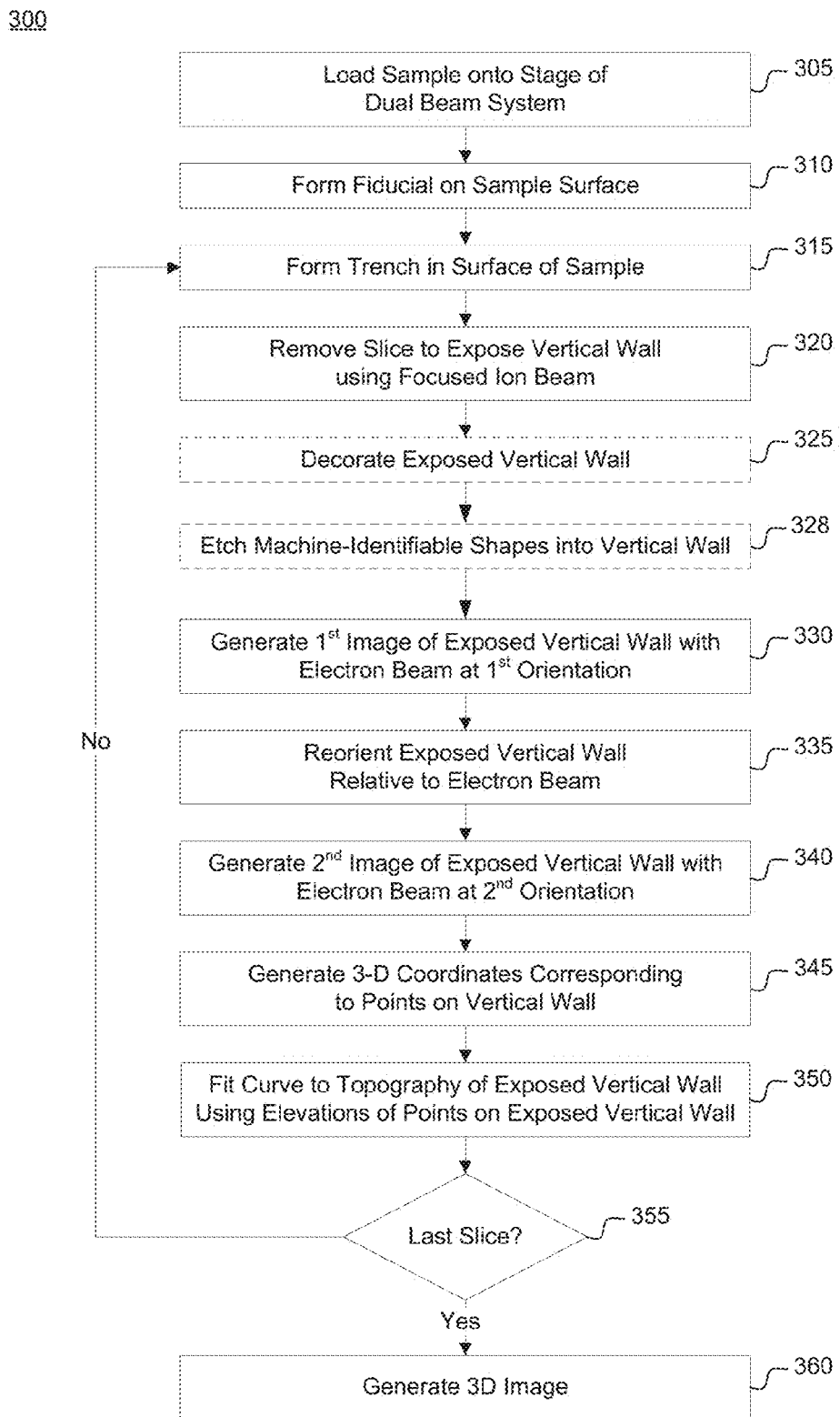
FIG. 3 is a flow diagram of a method of processing a sample by slice and view processing according to an embodiment of the disclosure.

Referring now to FIG. 3, a flow diagram of a method 300 of processing a sample by slice and view processing with a dual beam system in accordance with an embodiment of the disclosure is shown. In order to remove material from the sample, the dual beam system of method 300 utilizes an etching beam, such as a focused ion beam from a FIB device or a laser beam from a laser. In order to image surfaces of the sample exposed by the etching beam, the dual beam system of method 300 utilizes an interrogating beam, such as an electron beam from a SEM. In some embodiments, the sample is mounted on a stage. In some such embodiments, the stage is rotatable and/or translatable relative to the etching and interrogating beams, and rotation of the stage allows reorientation of the exposed surfaces such that images of the exposed surfaces can be taken from different perspectives. It should be noted that although the method 300 is explained using a focused ion beam from an FIB device, an electron beam from an SEM, a rotatable stage, and other specific elements, such selections are merely exemplary, and components capable of equivalent functions may be used. It should further be noted that while various embodiments of the disclosure utilize focused ion beams and/or lasers to remove slices, other tools, such as an ultramicrotome, could also be used for slice removal. Such tools may also form exposed surfaces deviating from a flat profile, which may be corrected for using one or more of the techniques disclosed herein.

The method 300 may begin at Block 305 by loading a sample onto the stage of the dual beam system. The stage of the dual beam system is typically tilted to 52 degrees from the horizontal so that the FIB impacts normal to the sample surface, and the electron beam impacts the sample surface at 52 degrees. In some embodiments, cross-sectional walls approximately perpendicular to the sample surface are achieved by having the focused ion beam impact the surface of the sample at a slight angle from the normal to account for the Gaussian shape of the focused ion beam cross-section. A stage tilt angle of 53 or 54 degrees can provide a more vertical cross-section wall than a stage tilt of 52 degrees.

Figure 4A:
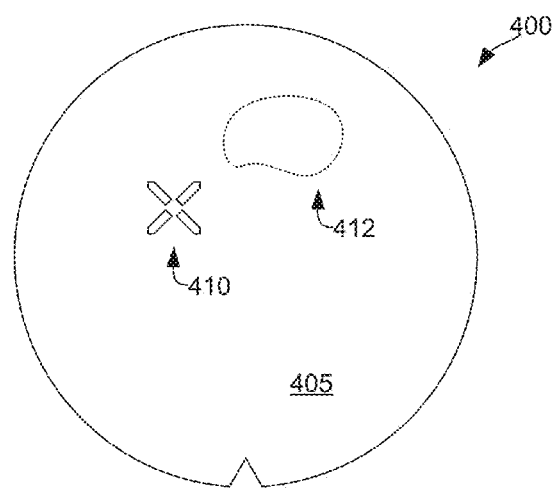
FIG. 4A is a simplified diagram of a sample provided with a fiducial in accordance with an embodiment of the disclosure.

The method 300 may continue to Block 310 by forming fiducial 410 in surface 405 of a sample 400 in proximity to feature 412 to be observed using the focused ion beam to facilitate accurate positioning of the focused ion and electron beams during slice and view processing. As shown in FIG. 4A, fiducial 410 is preferably of a robust shape so that the centerline of fiducial 410 is readily recognizable even after repeated scans by the focused ion beam, which tends to erode fiducial 410. In some embodiments, fiducial 410 may be formed sufficiently close to the location of the sample 400 slicing so that the stage does not need to be moved to shift the focused ion and electron beam positions from fiducial 410 to an area being removed. That is, the electron beam can be shifted sufficiently using beam deflection electrodes to image the fiducial 410 or to remove a cross section from the sample 400 without requiring a stage movement. Fiducial 410 is used to ensure accurate positioning of the focused ion beam and the electron beam in Blocks 315, 320, 325, 330, and 340. Beam position is obtained by re-imaging fiducial 410 to obtain new coordinate offsets to adjust the system for beam and stage drift. The coordinates of fiducial 410 are known, so any discrepancy between the known coordinates of fiducial 410 and the measured coordinates of fiducial 410 produce an offset that can be applied to the measured coordinates. In machines that have no edge recognition capability, local beam placement is performed solely using the fiducial 410 as a reference. Feature 412 may be below the surface, as shown by the dashed lines in FIG. 4A.

Figure 4B:
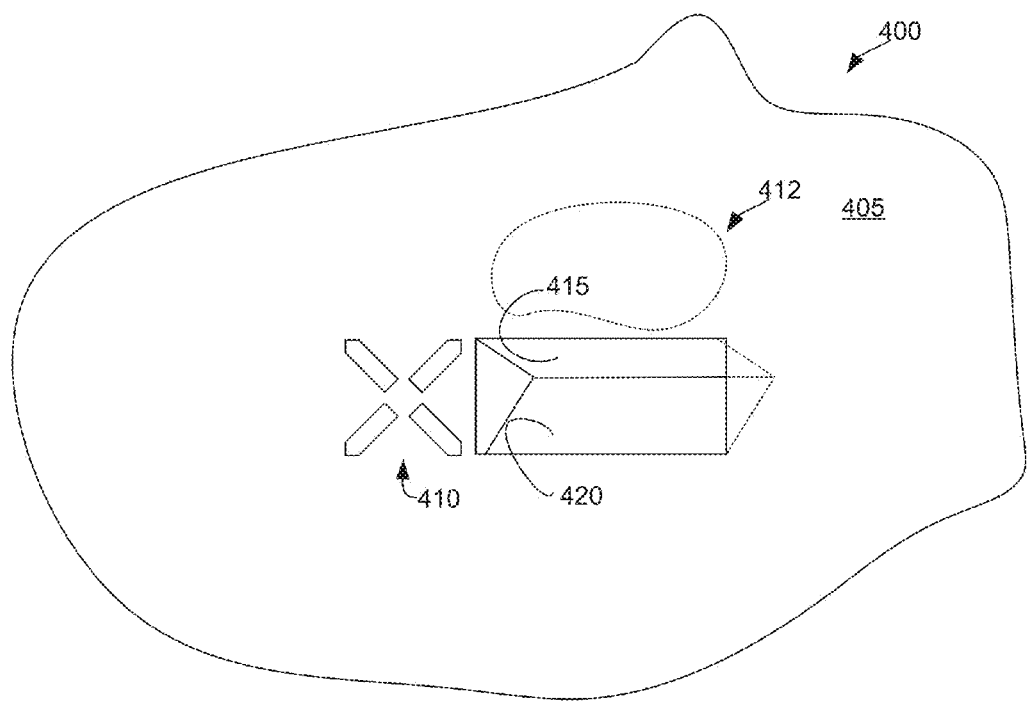
FIG. 4B shows an enlarged portion of the sample of FIG. 2A in which a sloping trench has been formed in a surface of the sample.

The method 300 may continue to Block 315 where sloping trench 420 (FIG. 4B) in surface 405 of sample 400 is formed using the focused ion beam. Sloping trench 420 may, for example, be milled approximately 1 μm from feature 412, have a width of about 4 microns, and a depth in a range of from about 1.0 μm to about 3.0 μm. The depth of the sloping trench 420 may depend on the position of feature 412 below the surface. The angle of the sloping trench 420 is sufficient so that both the focused ion beam and the electron beam can scan a cross section 415 at the end of sloping trench 420. Cross section 415 is typically normal to the substrate surface and runs parallel to the direction of the line mill. A thin, finishing cut may be made at cross section 415 to provide a smoother surface than was provided by the focused ion beam when the focused ion beam was removing the bulk of material to form sloping trench 420. In some embodiments, sloping trench 420 is dimensioned such that the electron beam may fully interrogate a vertical wall exposed by the FIB from two or more different orientations (of the SEM relative to the vertical wall to be imaged), without obstruction of the electron beam by other surfaces of the sample.

In various embodiments, the size and shape of the area to be milled is determined through information gathered by machine vision, which allows for accuracy and automation of the sample processing. In machine vision, a computer is used to process image information, usually obtained from the SEM image, to determine physical properties of a feature such as a feature's edges, size, and center of mass. Software used for machine vision may include, for example, Cognex VisionPro software from Cognex Corporation, Nantick, Mass. Typical machine vision software operates to identify a feature in a sample region based on image properties such as average gray level, contrast and texture. For instance, each pixel in the image may be given an assigned value, such as a single number, that represents a texture quality of that pixel with respect to surrounding pixels. The feature of interest will typically have different image properties, such as texture, from the surrounding sample in which the feature is imaged. The feature of interest therefore can be identified as the group of pixels having an average texture within a certain parameter of value that differs from the surrounding image. The machine vision software preferably automatically locates and measures the feature of interest in each imaged slice of the sample.

Figure 2A:
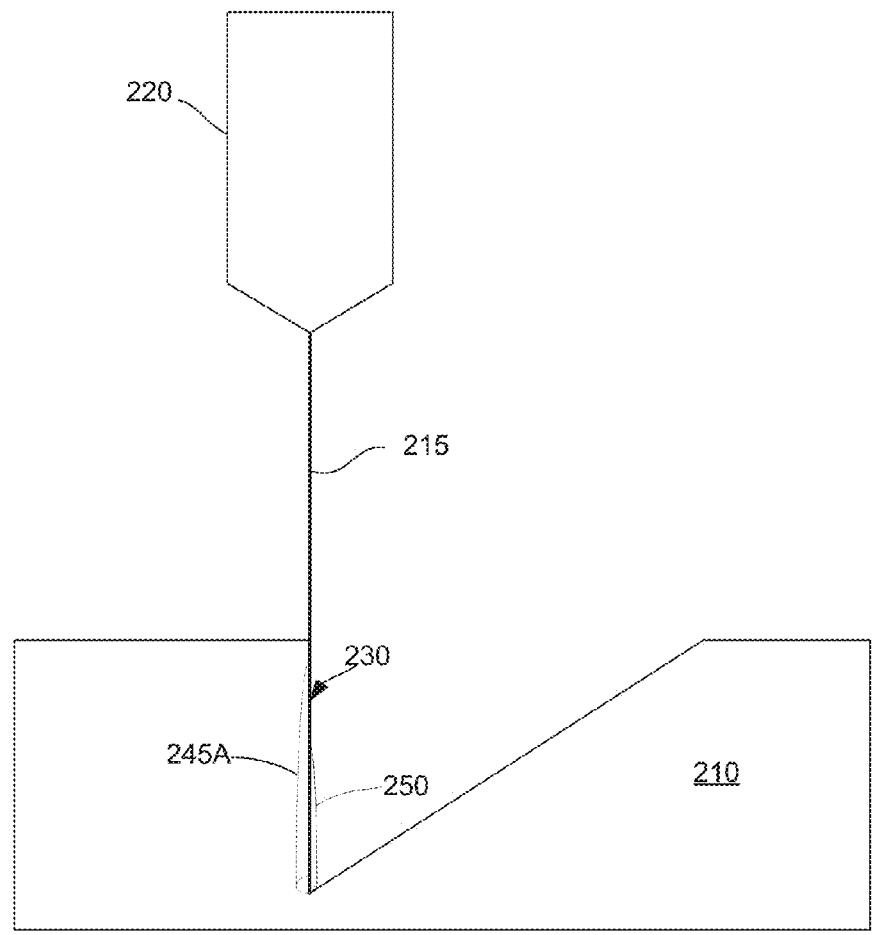
FIG. 2A is a side view diagram of a sample undergoing slice and view processing and exhibiting curtains.
Figure 2B:
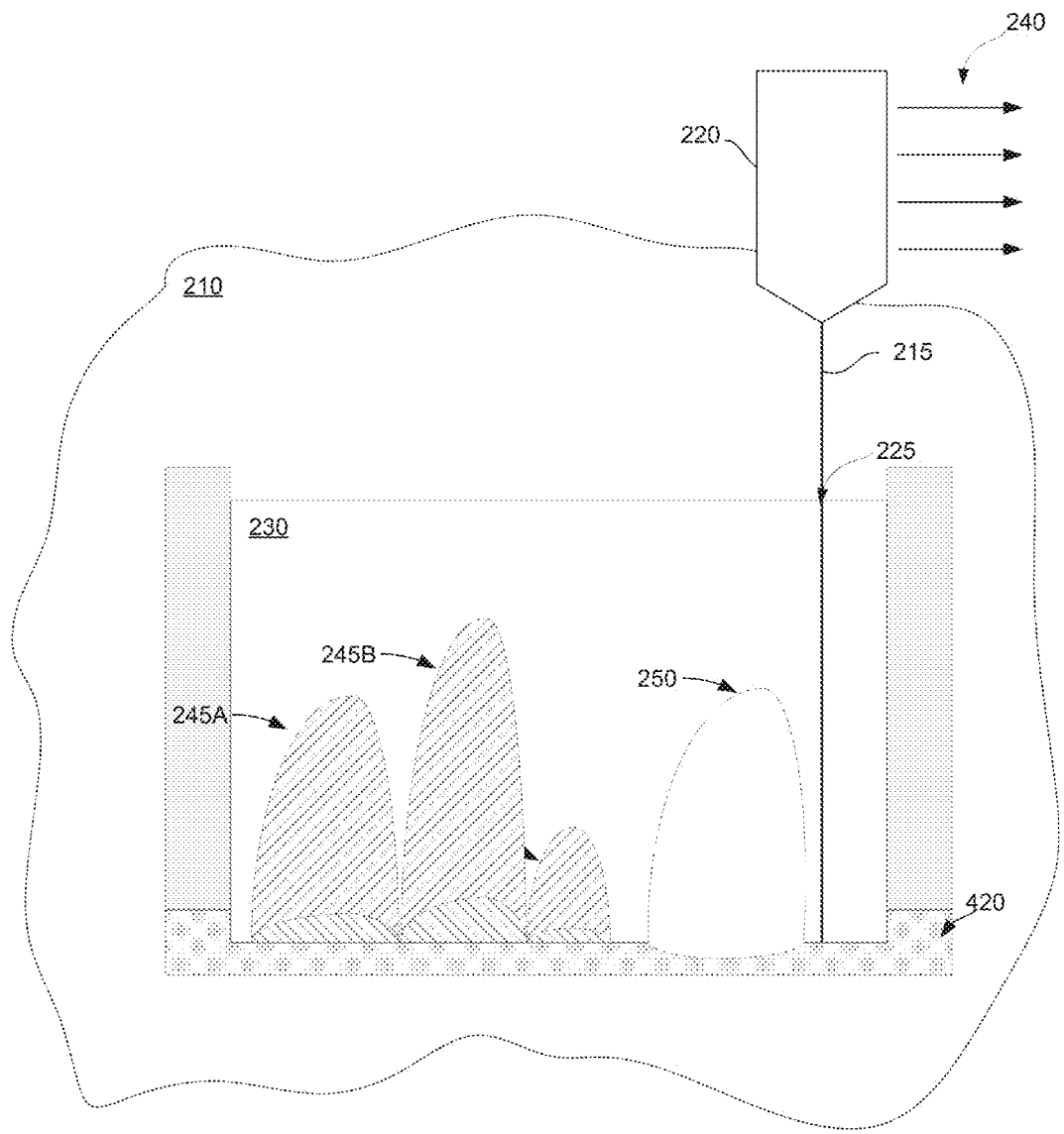
FIG. 2B is a front elevated view diagram of the sample of FIG. 2A.
Figure 5:
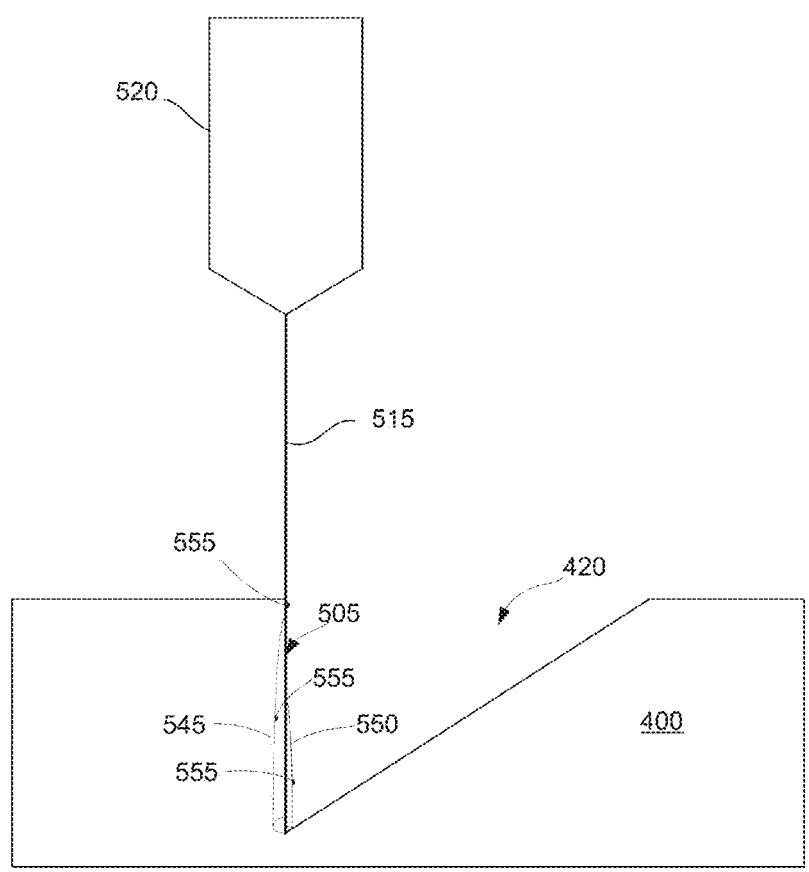
FIG. 5 is a simplified diagram showing the execution of a line mill by a focused ion beam to expose a surface of a sample in accordance with an embodiment of the disclosure.

The method 300 may continue to Block 320 where, as shown in FIG. 5, a vertical wall 505 having curtaining artifacts 545 and 550 is exposed by removing a slice of material from sloping trench 420 across cross-section 415. The slice of material may be removed from sloping trench 420 using a focused ion beam 515 from FIB column 520. In some embodiments, the slice of material is removed by executing a "line mill," as is shown in FIG. 5. A line mill involves milling an essentially one dimensional line running substantially parallel to the plane of a cross-section 415 (and vertical wall 505). The execution of a line mill is A line mill is also illustrated in FIGS. 2A and 2B, wherein focused ion beam 220 of FIB column 220 carrying out line mill 225 by traversing face 230 of sample 210 from left to right in a straight line in the direction of arrows 240, focused ion beam 215 being substantially parallel to face 230. In other embodiments, the slice of material is removed by executing a rectangle mill with focused ion beam 515. In one such embodiment, FIB column 520 is part of a system configured to receive input from a user specifying a slice thickness and remove slices of material of the specified thickness by executing a line mill with a focused ion beam from FIB column 520.

In various embodiments, the thickness of slice removed by the etching beam (focused ion beam 515 in the case of FIG. 5) is in a range of from about 20 nm to about 100 nm, such as in a range of from about 30 nm to about 60 nm, alternatively from about 35 nm to about 45 nm, alternatively from about 35 nm to about 40 nm. In some embodiments, thickness of the milled slice removed may be less than about 300 nm. The width and height dimensions of the slice removed may be, for example, in a range of from about 10 μm to about 100 μm.

In some embodiments, the method 300 may initially skip Block 320. In such embodiments, Blocks 325-355 are first carried out with respect to the surface of the sample exposed at cross-section 415 in Block 315. In such embodiments, the first iteration of Block 320 will be carried out on the second surface imaged in the slice and view processing of sample 400.

The method 300 may optionally include Block 325 where the surface of vertical wall 505 is decorated. As used herein, the term "decorating" refers to the light preferential etching of portions of a surface of the sample, such as vertical wall 505, to delineate interfaces between layers, as described, for example, in U.S. Pat. No. 7,858,936 to Castagna and Bray for "Slice and View with Decoration," which is owned by the application of the present invention.

In step 328, machine-identifiable shapes are optionally etched into the vertical wall to mark or flag the location of surface points 555 on vertical wall 505. In some embodiments, forming the machine-identifiable shapes may be carried out by an electron beam directed toward vertical wall 505 in the presence of an etch-enhancing gas, such as xenon difluoride. The electron beam and gas preferentially etches some of the materials present on vertical wall 505, so that the same surface points 555 can be identified in images of the vertical wall 505 captured from different viewing angles (e.g., at a different angle of incidence of the interrogating beam). For example, xenon difluoride etches silicon oxides faster than it etches silicon nitrides and so leaves a small stair-step edge at the oxide-nitride boundary. The thickness of material removed may, for example, be less than about 30 nm, alternatively less than about 20 nm. In some embodiments, the depths of the machine-identifiable shapes are preferably smaller than the slice thickness, so that the shapes are milled away with each slice. In other embodiments, the shapes may be milled deeper that the slice thickness so that the points are visible from slice-to-slice to make the same points on different slices. The shapes can be re-milled at each slice, optionally to a depth greater than the slice thickness to propagate the point through a series of slices.

Machine identifiable shapes can be formed at positions on the vertical wall that appear from the image to have different elevations, as determined either manually by an operator or automatically using image recognition software. Alternatively, machine-identifiable shapes could be milled in a regular pattern, such as a rectangular rid across the surface. In some embodiments, rather than using a milled machine-identifiable shapes, existing sample features can be used, or a combination of existing features and milled shaped. A pattern of points to form an elevation map of the vertical face can be determined by using offsets from one or more machine identifiable features or fiducials, without each of the measurement points being individually marked. For example, a positioning and orienting fiducial can be milled in one corner of the sample, and then the elevation can be determined at points in a grid pattern, with the points spaced at known distances from the fiducial in an x-ray array, or other pattern.

Figure 6A:
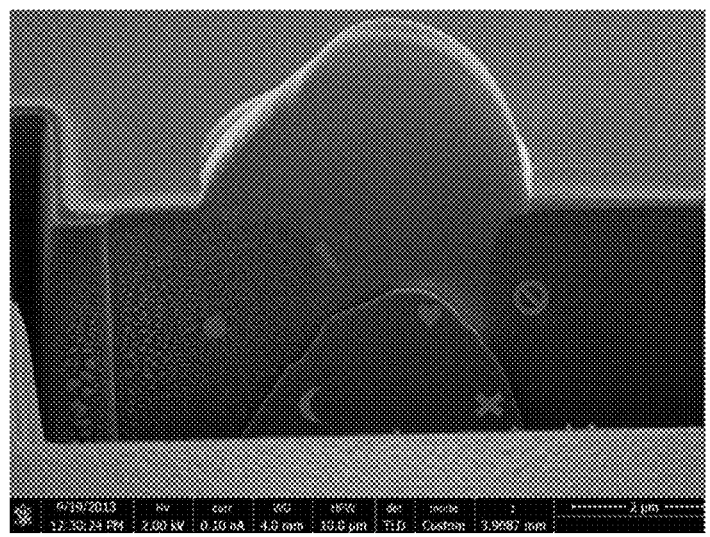
FIG. 6A shows an SEM micrograph of a sample captured by an electron beam while maintaining the sample at a first orientation and having machine-recognizable shapes that can be etched at various points into the face of the sample.
Figure 6B:
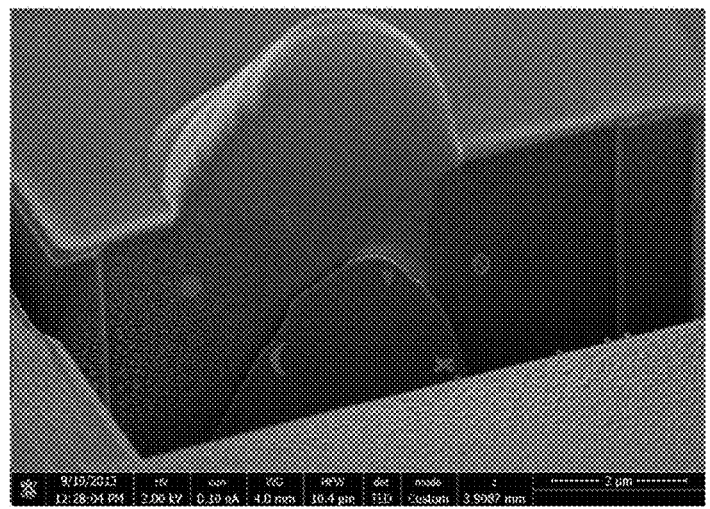
FIG. 6B shows an SEM micrograph of the sample of FIG. 6A captured while maintaining the sample at a second orientation different from the first orientation in accordance with an embodiment of the disclosure.

The presence of machine-identifiable shapes on vertical wall 505 improves the ability of machine vision software to identify the position of specific surface points 555 on vertical wall 505 in images of the sample captured by the SEM at different angles of incidence. Referring to FIGS. 6A and 6B, SEM micrographs of a face of a sample exposed by a focused ion beam have been captured by an electron beam while maintaining the exposed vertical wall at different orientations relative to the electron beam. To illustrate how machine-identifiable shapes may be used to identify the location of specific surface points 555 on the face in different images captured at different orientations, graphics of six different machine-identifiable shapes have been superimposed over each micrograph at positions corresponding to specific locations on the sample face. The machine-identifiable shapes of FIG. 6B have further been edited to show how the machine-identifiable shapes would appear if rotated and imaged with the actual sample of the micrograph. Although the degree of orientation has distorted the images of FIG. 6B, the specific positions marked by the machine-identifiable shapes are instantly identifiable to the human eye. By comparison, points surrounding some of the machine-identifiable shapes (e.g., the ∦ and ⊘ machine-identifiable shapes) lie on relatively featureless planes of the sample, and are considerably more difficult to track between images captured at different orientations and to distinguish from nearby points that are also located on the relatively featureless plane.

Machine-identifiable shapes suitable for various embodiments of the disclosure typically comprise substantially 2-D shapes identifiable by pattern recognition algorithms of machine vision software. Examples of suitable machine-identifiable shape shapes include, but are not limited to, basic geometric shape, such as circles, squares, triangles, and rectangles, and simple symbols, such those shown in FIGS. 6A-6B, 8A-8B, and 9B-9C. Varying the shape of machine-identifiable shapes used for surface points 555 reduces or eliminates the likelihood that a decorated point shown in a first image of vertical wall 505 will be mistaken for a different point marked with a machine-identifiable shape having an identical or similar shape as the decorated point in a second image captured after reorienting the beam relative to vertical wall 505. A greater diversity of shapes used to mark surface points 555 will result in a lower likelihood of misidentification. In an embodiment, machine-identifiable shapes used to identify surface points 555 on vertical wall 505 comprise at least two shapes.

Figure 7A:
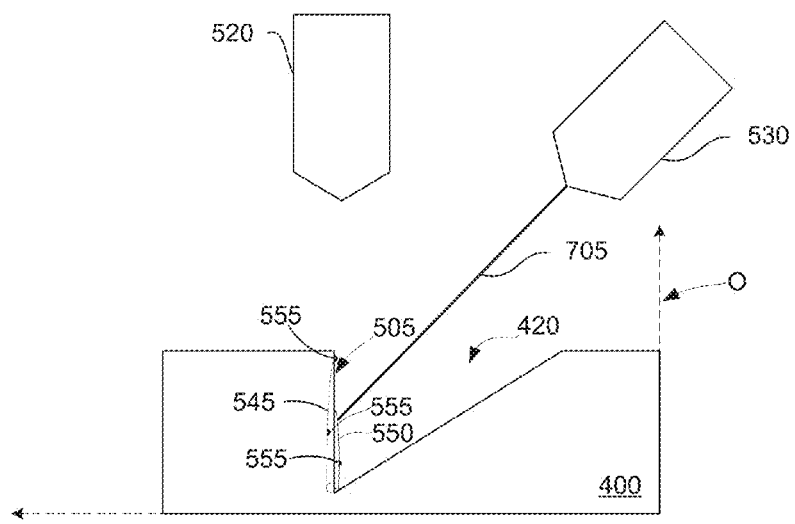
FIGS. 7A-7C are diagrams illustrating the imaging of a sample surface by a SEM device from two different orientations in accordance with an embodiment of the disclosure.

From Block 325, the method 300 may continue to Block 330 by capturing and storing a first image of vertical wall 505 with an electron beam of an SEM while vertical wall is maintained at a first orientation relative to the electron beam and/or the SEM. As shown in FIG. 7A, a first image of vertical wall 505 may be generated by interrogating vertical wall 505 of sample 400 with electron beam 705 from SEM 530 as vertical wall 505 is held at a first orientation "O" relative to electron beam 705. The electron beam 705 is typically operated at 5 kV and uses a through-the-lens detector. Storage of images capture by electron beam 705 may be implemented on a computer-readable storage medium such as a computer hard drive.

From Block 330, the method 300 may continue to Block 535 by reorienting the vertical wall 505 relative to electron beam 705 and/or SEM 530 from the first orientation O to a second orientation "O'." Reorientation of vertical wall 505 relative to electron beam 705 may be carried out by rotating or tilting sample 400. Additionally or alternatively, reorientation of vertical wall 505 relative to electron beam 705 may be carried out by changing an angle of incidence between electron beam 705 and the vertical wall 505 by translating the SEM 530 away from the longitudinal axis 710 of the SEM 530 maintained during the capturing of the first image. In both orientation O and κ', SEM 530 is aligned such that longitudinal axis 710 intersects vertical wall 505.

Figure 7B:
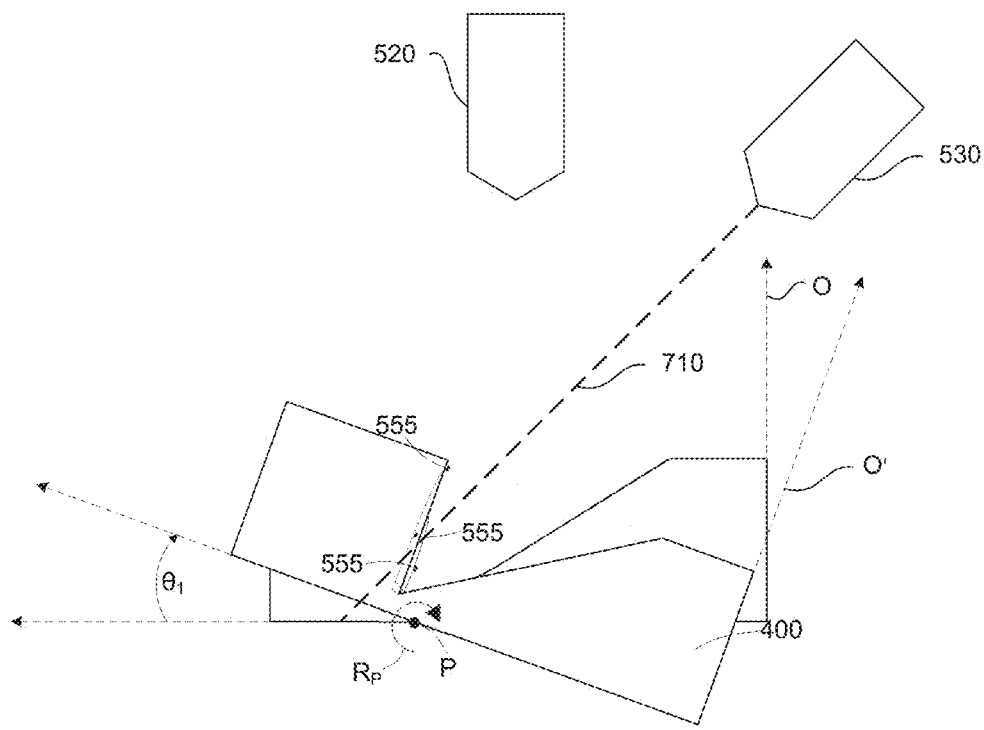
Figure 7C:
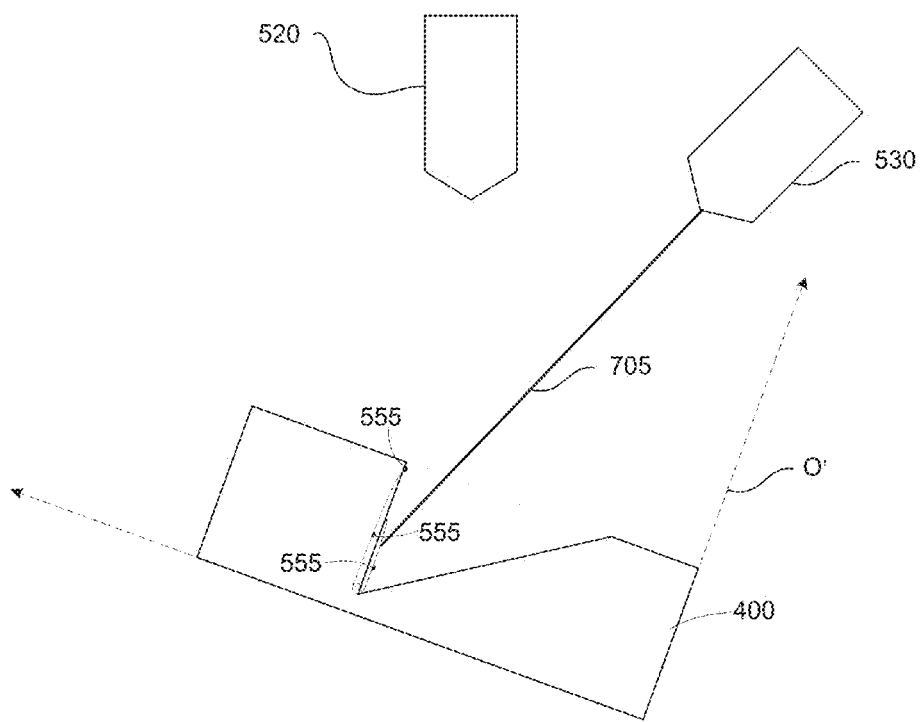

Referring now to FIG. 7B, a diagram illustrating a reorientation of vertical wall 505 relative to SEM 530 according to an embodiment of the disclosure is shown. Reorientation of vertical wall 505 is carried out by tilting sample 400 by an angle $\theta_1$ in the direction of arrow Rp about an axis normal to the viewing plain (shown as point P). The reorientation changes the orientation of sample 400 from orientation O to orientation O'. After reorientation of vertical wall 505, the method 300 may continue to Block 340 by capturing and storing a second image of vertical wall 505 at orientation O'. As shown in FIG. 7C, the second image of vertical wall 505 may be generated by interrogating vertical wall 505 of sample 400 with electron beam 705 from SEM 530 as vertical wall 505 is held at a first orientation O' relative to electron beam 705.

In various embodiments, imaging of vertical walls 505 is carried out using focused ion beam 515 of FIB column 520. In some embodiments, the imaging steps of method 300 are carried out using the FIB column 520, and a SEM is not used to capture the images of vertical walls 505. In one such embodiment, a single charged particle beam may be used instead of a dual charged particle beam system. In other embodiments, both FIB column 520 and SEM 530 are used to capture the images of vertical walls 505. In some embodiments, one or more of the vertical walls may be imaged by both FIB column 520 and SEM 530. In some embodiments, one or more vertical walls are imaged by both FIB column 520 and SEM 530 while one or more other vertical walls are imaged by only one of FIB column 520 and SEM 530. In some embodiments, one or more vertical walls are imaged by both FIB column 520 and SEM 530 while the other vertical walls are imaged by FIB column 520 but not SEM 520, or by SEM 530 but not FIB column 520.

From Block 340, the method 300 may continue to Block 345, wherein 3-D coordinates corresponding to surface points 555 are generated. In an embodiment, the 3-D coordinates for a given surface point $p_i$ of surface points 555 comprise the x and y coordinates of the point $p_i$ on the imaging plane (see e.g., FIG. 1) of vertical wall 505, as measured from an arbitrary origin, and the elevation of the point $p_i$.

Differences in elevations of surface points 555 on vertical wall 505 may be determined using the first and second images captured by SEM 530 at orientations O and O', respectively. One point can be designated being positioned in a reference plane from which other elevations are measured. An elevation $Z_i$ for a given surface point $p_i$ of surface points 555 may be determined by measuring the distances between surface point $p_i$ and a fixed reference point in each of the first and second images, and inputting the measured distances into the following Formula (1):

$$Z_i = \frac{|\overline{A_i'B_i'}| - |\overline{A_iB_i}|\cos\theta}{\sin\theta},\quad \text{Formula (1)}$$

Wherein
$A_i$ is a position of the reference point in the first image, $A_i'$ is a position the reference point in the second image, $B_i$ is a position of point i in the first image, $B_i'$ is a position of point i in the second image, $Z_i$ is the elevation relative to the height at reference point $A_i$ of surface point i, at position $B_i$, $|\overline{A_i'B_i'}|$ is the distance between $A_i'$ and $B_i$, $|\overline{A_iB_i}|$ is the distance between $A_i$ and $B_i$, and $\theta$ is the difference of the first angle of incidence and the second angle of incidence.

The relationship between the capturing of the first image of vertical wall 505 of Block 330, the reorienting of vertical wall 505 of Block 335, the capturing of the second image of vertical wall 505 of Block 340, and the variables of Formula (1) may be better understood from the embodiments of the disclosure shown in FIGS. 8A-9C. It the outset, it should be understood and observed by comparing FIG. 9C to FIG. 9B and FIG. 8A to FIG. 8B, that the distances between one or more pairs of points on a vertical wall 405 measured in the first image of the vertical wall 405 differ from distances measured for the same pairs of points when measured in the second image of vertical wall 405.

Figure 8A:
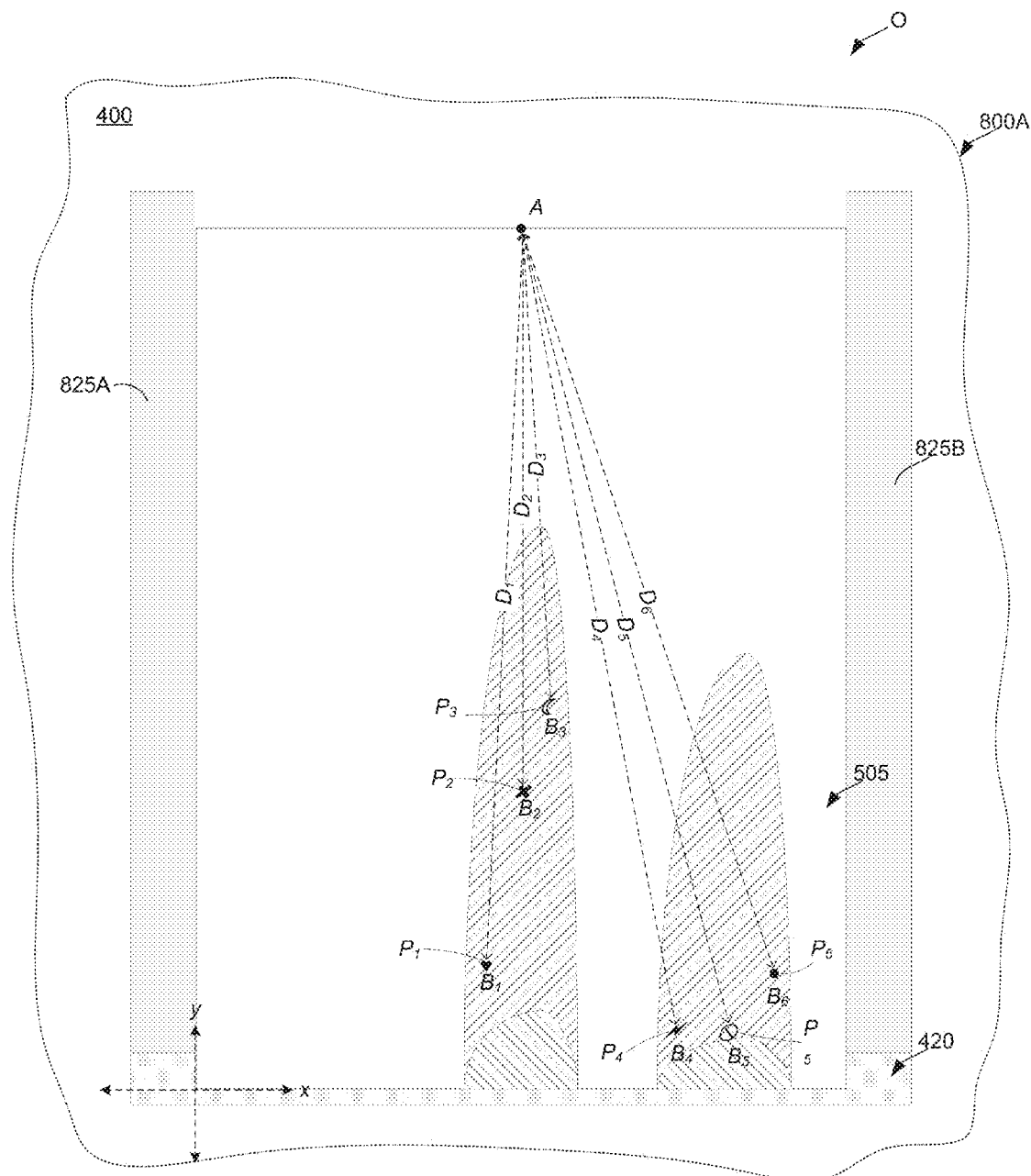
FIGS. 8A and 8B are schematic illustrations of SEM images of a sample surface captured by a SEM in accordance with an embodiment of the disclosure.
Figure 8B:
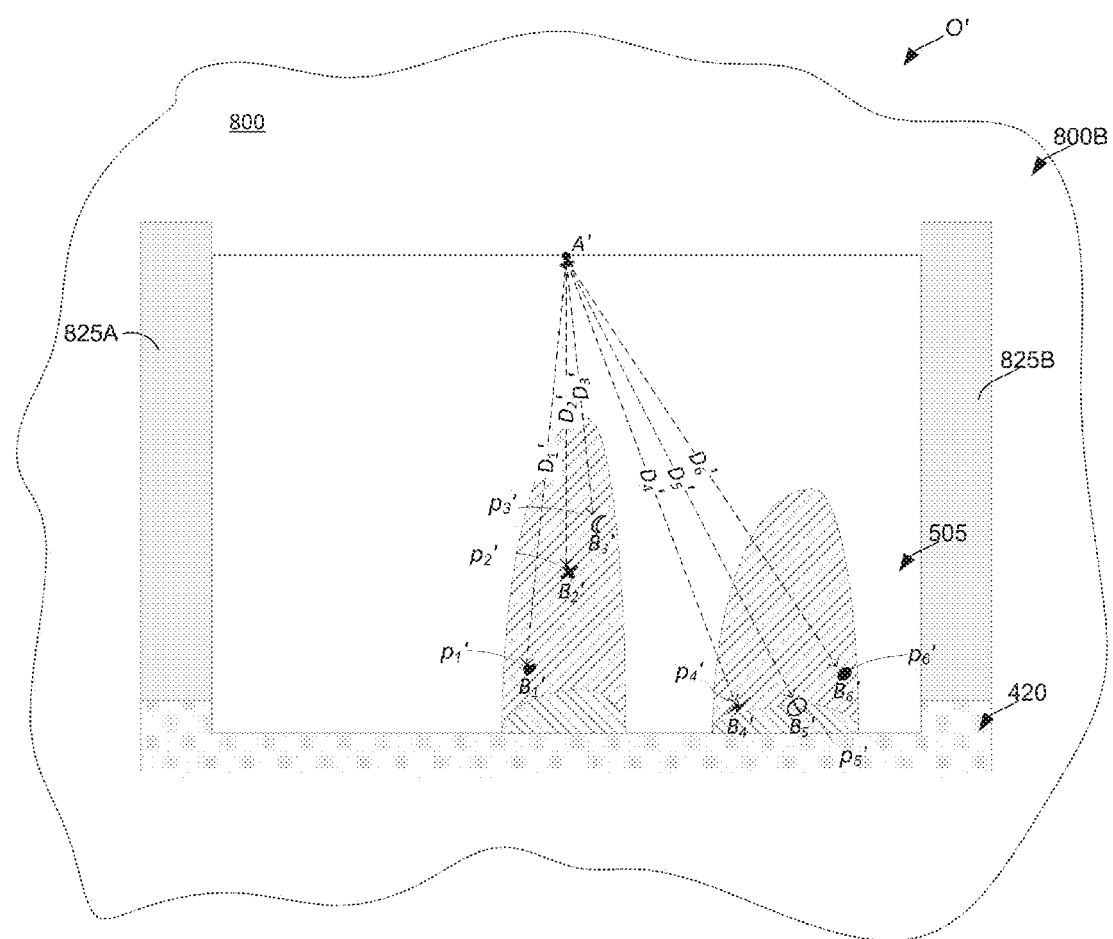

In FIGS. 8A and 8B, SEM images have been captured for vertical wall 505 after being decorated by focused ion beam 515. In FIG. 8A, SEM image 800A shows vertical wall 505 imaged by SEM 530 from the orientation O shown in FIG. 7A. Machine-identifiable shapes $B_1$, $B_2$, $B_3$, $B_4$, $B_5$, and $B_6$ mark the location of points $P_1$, $P_2$, $P_3$, $P_4$, $P_5$, and $P_6$, respectively. Each of distances $D_1$, $D_2$, $D_3$, $D_4$, $D_5$, and $D_6$ correspond to the values for the expression $|\overline{A_iB_i}|$ of Formula (1) for points $P_1$, $P_2$, $P_3$, $P_4$, $P_5$, and $P_6$, respectively. As described above, various embodiments of the disclosure utilize machine vision to locate features of images captured in method 300, and, when used in combination with machine-identifiable shapes such as the machine-identifiable shapes $B_1$, $B_2$, $B_3$, $B_4$, $B_5$, and $B_6$, the accuracy of tracking surface points can be improved. For image 800A, machine vision may be used in combination with machine-identifiable shapes $B_1$, $B_2$, $B_3$, $B_4$, $B_5$, and $B_6$ to precisely determine the positions of points $P_1$, $P_2$, $P_3$, $P_4$, $P_5$, and $P_6$, allowing the x-y coordinates of points $P_1$, $P_2$, $P_3$, $P_4$, $P_5$, and $P_6$ and the distances $D_1$, $D_2$, $D_3$, $D_4$, $D_5$, and $D_6$ between $P_1$, $P_2$, $P_3$, $P_4$, $P_5$, and $P_6$ and reference point A to be precisely determined. Further, as discussed above, machine vision improves the tracking of points between images of vertical wall 505 taken at different orientations, such as between image 800A and 800B, by reducing the probability of mistaking the identity of one surface point for another.

Turning to FIG. 8B, SEM image 800B shows vertical wall 505 imaged by SEM 530 from the orientation O' shown in FIG. 7A. Machine-identifiable shapes $B_1'$, $B_2'$, $B_3'$, $B_4'$, $B_5'$, and $B_6'$ mark the location of points $P_1'$, $P_2'$, $P_3'$, $P_4'$, $P_5'$, and $P_6'$, respectively. Each of distances $D_1'$, $D_2'$, $D_3'$, $D_4'$, $D_5'$ and $D_6'$ corresponds to the values for the expression $|\overline{A_iB_i}|$ of Formula (1) for points $P_1$, $P_2$, $P_3$, $P_4$, $P_5$, and $P_6$, respectively. Similar to FIG. 800A, machine vision may be used to more precisely ascertain the values of $D_1'$, $D_2'$, $D_3'$, $D_4'$, $D_5'$ and $D_6'$. Machine vision, used in combination with the five uniquely shaped machine-identifiable shapes $B_1$, $B_2$, $B_3$, $B_4$, $B_5$, and $B_6$ may also be used to identify the points $P_1'$, $P_2'$, $P_3'$, $P_4'$, $P_5'$, and $P_6$ so that elevations $Z_1$, $Z_2$, $Z_3$, $Z_4$, $Z_5$, and $Z_6$ are not inadvertently calculated using distances from the wrong points. It should be noted that points $P_1$-$P_6$ and $P_1'$-$P_6'$ correspond to the same locations on vertical wall 505 exposed by focused ion beam 515 and imaged by SEM 530 and that points $P_1$-$P_6$ and $P_1'$-$P_6'$ are the representations of those locations as viewed in SEM images 800A and 800B. Likewise, reference points A and A' also correspond to the same location on sample 400. Referring again to FIGS. 7A-7C, the angle $\theta$ of Formula (1) used for calculating the elevations $Z_1$, $Z_2$, $Z_3$, $Z_4$, $Z_5$, and $Z_6$ is angle $\theta_1$ shown in FIG. 7B.

In some embodiments, to facilitate unobstructed access of electron beam 705 to vertical wall 505 at larger values of angle $\theta$, side trenches 825A and 825B may be milled by focused ion beam 515 in Block 315 or as part of any one of Blocks 330, 335, and 340. For example, if reorientation of vertical wall 505 results in an orientation O' wherein access to vertical wall 505 is blocked be an obstructing portion of the sample, focused ion beam may be utilized to remove the obstruction to allow imaging of the entire vertical surface 505.

Figure 9A:
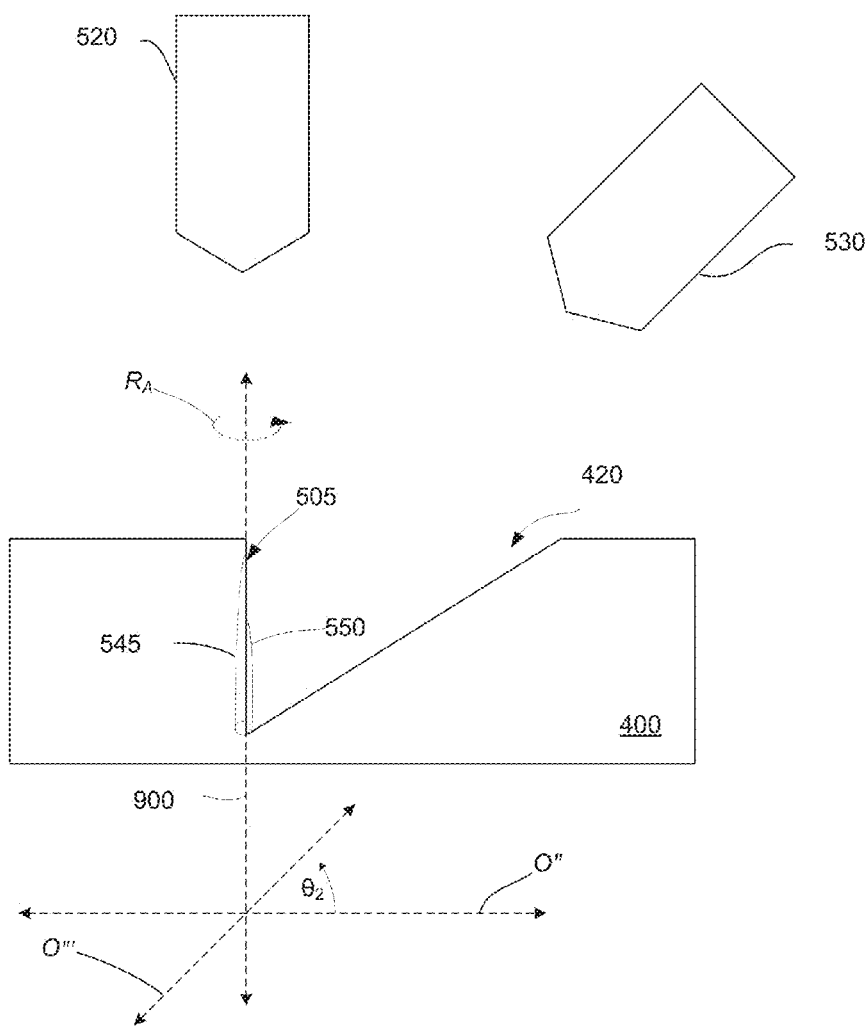
FIG. 9A, is a diagram illustrating the reorientation of a sample surface being imaged by an SEM from a first orientation to a second orientation according to another embodiment of the disclosure.
Figure 9B:
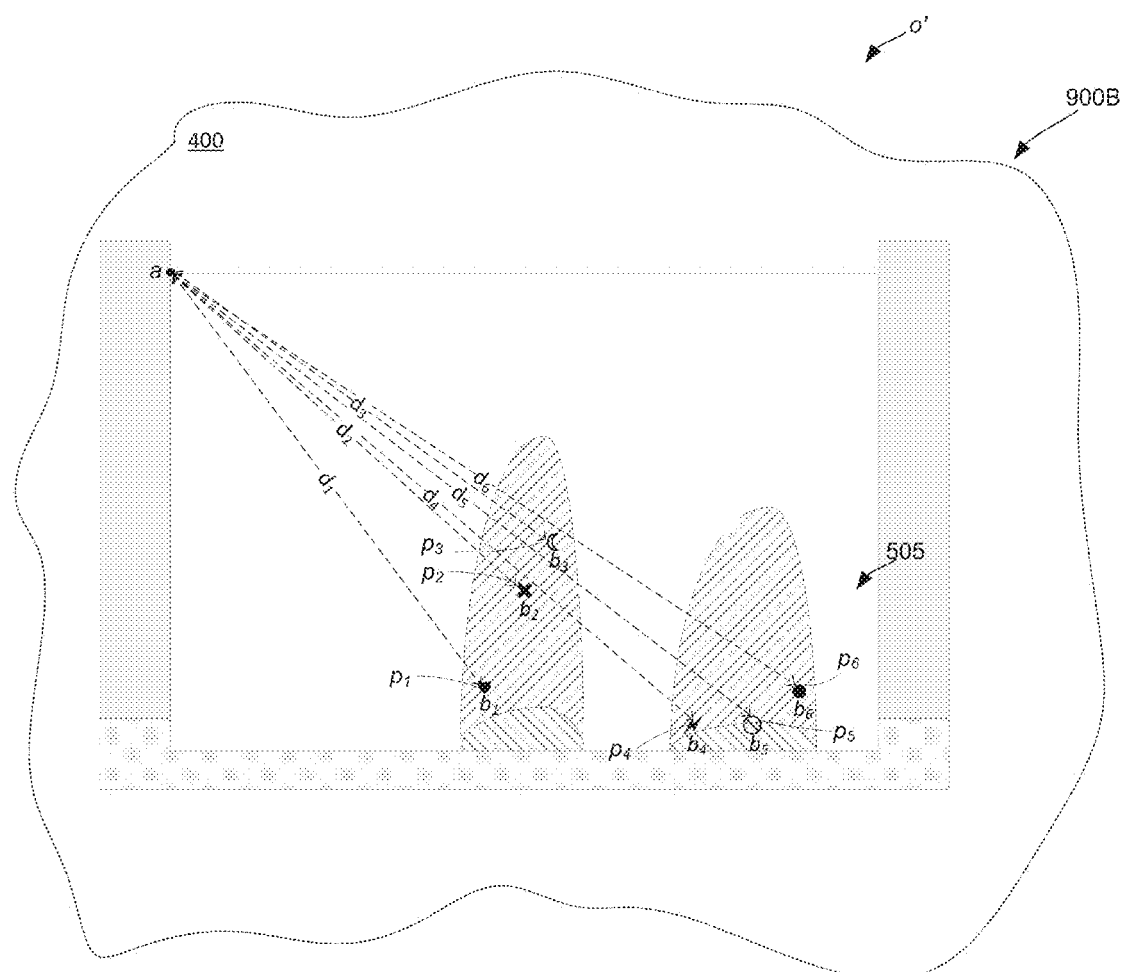
FIG. 9B is an illustration of a first image of the sample surface of FIG. 9A captured by an SEM while the sample surface is maintained at a first orientation relative to the SEM.
Figure 9C:
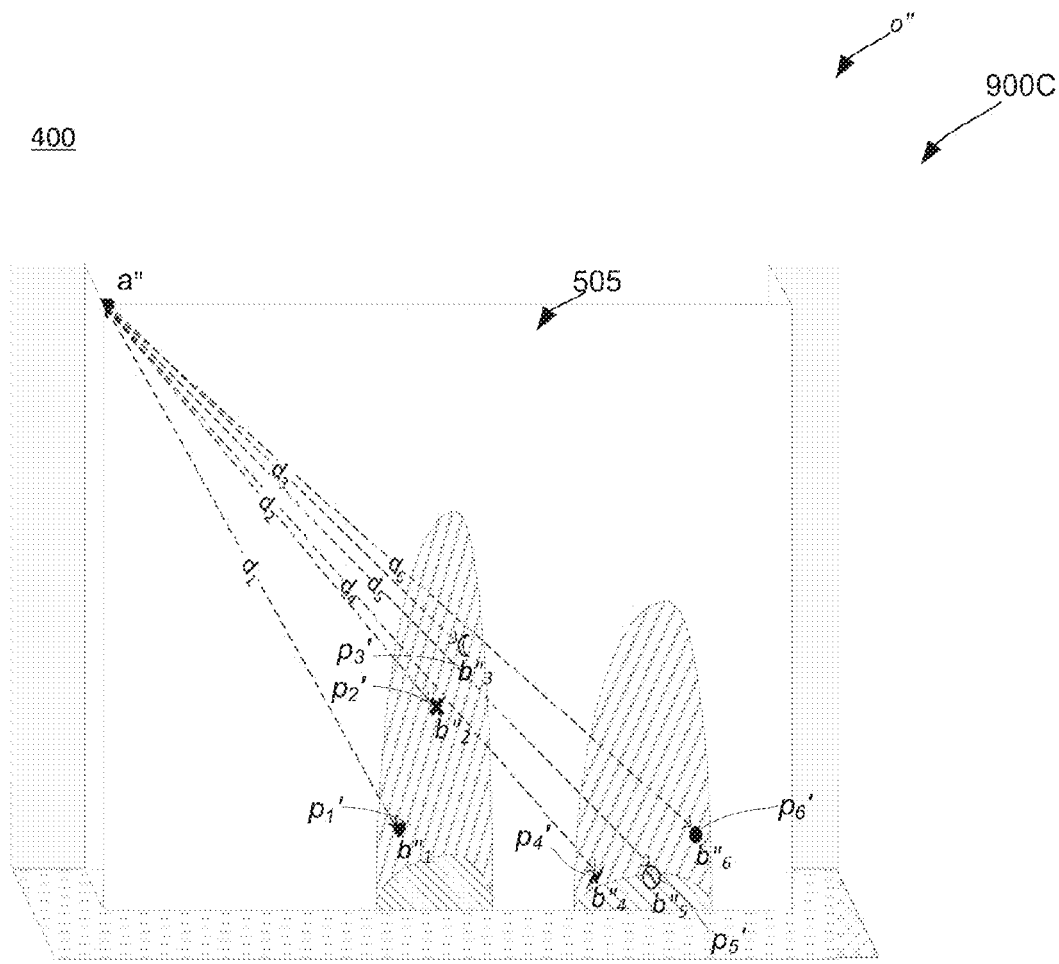
FIG. 9C is an illustration of a second image of the sample surface of FIG. 9A captured by an SEM while the sample surface is maintained at a second orientation relative to the SEM.
Figure 10:
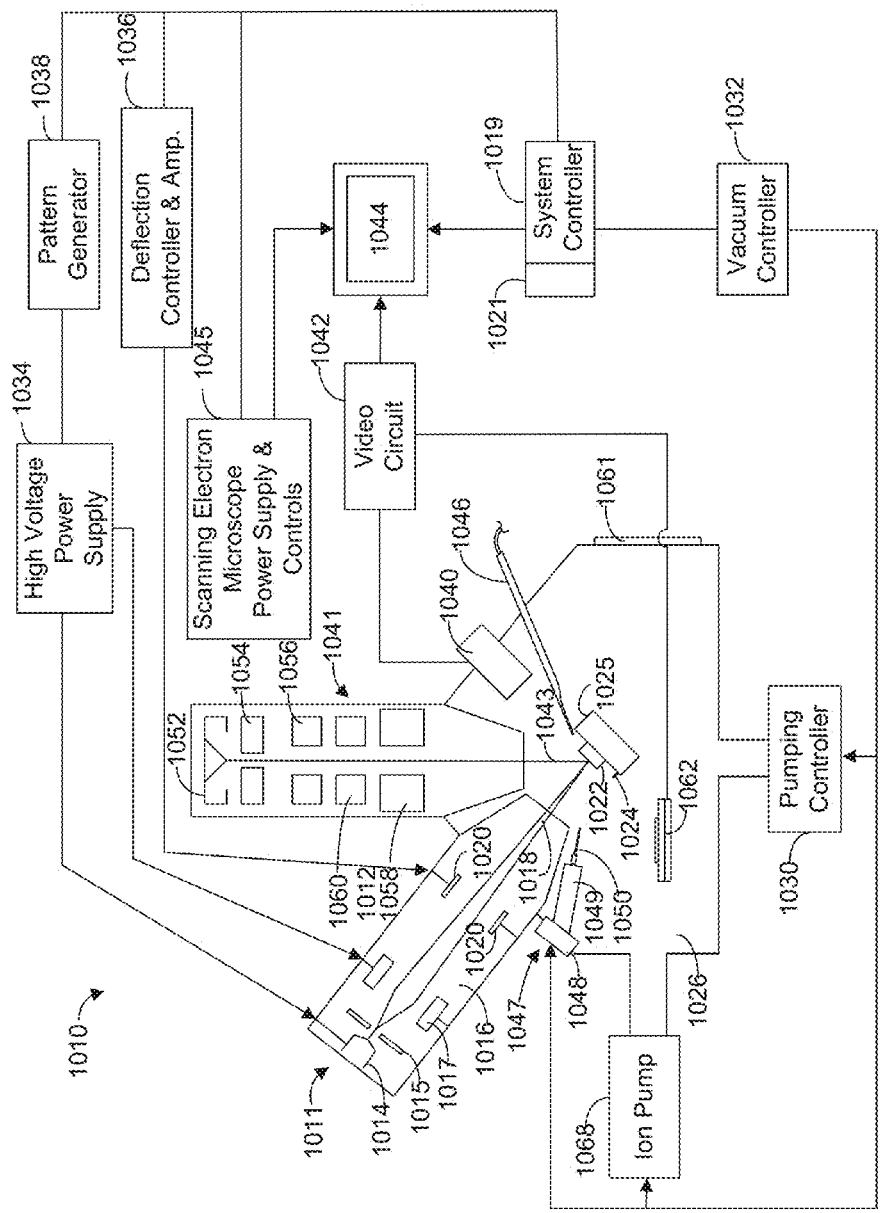
FIG. 10 is a schematic diagram of an apparatus for observing a feature using dual charged particle beams according to an embodiment.

The orientation of vertical wall 505 relative to the electron beam 705 and/or the SEM 530 is not limited to the rotations shown in FIGS. 7A and 7B, and the method 300 contemplates the use of any translation of vertical wall 505 relative to SEM 530 whereby topographical information can be extracted from images of vertical wall 505 obtained in accordance with Blocks 330 and 340. One such embodiment is illustrated in FIGS. 9A-9C. FIG. 9A shows a decorated vertical wall 505 situated at an orientation o'. In FIG. 9A vertical wall 505 is rotated from orientation o' about axis 900 by an angle $\theta_2$ in the direction of rotation indicated by arrow $R_4$ to an orientation o". Axis 900 overlaps or runs parallel to the longitudinal beam axis of FIB column 520. Illustrations of SEM images captured by SEM 530 at orientation o' and o" are shown in FIGS. 9B and 9C, respectively.

In FIG. 9B, SEM image 900A shows vertical wall 505 imaged by SEM 530 while vertical wall 505 is maintained at orientation o' relative to SEM 530. Machine-identifiable shapes $b_1$, $b_2$, $b_3$, $b_4$, $b_5$, and $b_6$ mark the location of points $p_1$, $p_2$, $p_3$, $p_4$, $p_5$ and $p_6$ on vertical wall 505, respectively. Each of distances $d_1$, $d_2$, $d_3$, $d_4$, $d_5$, and $d_6$ correspond to the values for the expression $|\overline{A_iB_i}|$ of Formula (1) for points $P_1$, $p_2$, $p_3$, $p_4$, $p_5$, and $p_6$, respectively. In FIG. 9C, SEM image 900C shows vertical wall 505 imaged by SEM 530 from the orientation o" shown in FIG. 9A. Machine-identifiable shapes $b_1'$, $b_2'$, $b_3'$, $b_4'$, $b_5'$ and $b_6'$ mark the location of points $p_1'$, $p_2'$, $p_3'$, $p_4'$, $p_5'$, and $p_6'$ on vertical wall 505, respectively. Each of distances $d_1'$, $d_2'$, $d_3'$, $d_4'$, $d_5'$ and $d_6'$ corresponds to the values for the expression $|\overline{A_iB_i}|$ of Formula (1) for points $p_1$, $p_2$, $p_3$, $p_4$, $p_5$, and $p_6$, respectively. Machine vision may be used to more precisely ascertain the values of $d_1'$, $d_2'$, $d_3'$, $d_4'$, $d_5'$ and $d_6'$. Referring again to FIG. 9A, the angle $\theta$ of Formula (1) used for calculating the elevations $z_1$, $z_2$, $z_3$, $z_4$, $z_5$ and $z_6$ is angle $\theta_2$.

Although all of the surface points of FIGS. 8A-9C are measured with respect to a single reference point, embodiments of the disclosure are not so limited. Distances may be measured for all of surface points 555 using a single reference, a different reference point for each of surface points 555, or distances for some of surface points 555 may be calculated from one or more common reference points and distances for other surface points may be calculated from unique reference points. Positions for the reference points may be any location on or above the sample that is visible in both the first image and the second image of the surface point 555 being imaged. In various embodiments, reference points and the surface points 555 are located on vertical surface 505. In one such embodiment, a single reference point located in corner of vertical wall 555 is used to calculate all of the elevations for surface points 555.

In Block 345, the references points, surface points 555, or both the reference points and surface points 555 may be randomly generated by system 1102, selected by a human operator, selected to facilitate more precise curve fittings, selected to satisfy a desired balance between speed of sample processing and precision of curve fittings, or any combination thereof. Unless prohibited by the constraints of a particular application, selection and/or machine-identifiable shape of the reference points and the surface points 555 may be carried out at any time after formation of the trench in Block 315 and before the destruction of vertical wall 505 by removal of the next slice of material in the next iteration of method 300. Selection and machine-identifiable shape of either of the reference points of surface points 555 may be carried out at the same time or at different times.

From Block 345, the method may proceed to Block 350 wherein curves are fitted to the 3-D coordinates to approximate a topography of vertical wall 505. In an embodiment, a topography of vertical wall 505 is approximated by applying a three-dimensional Fourier fit to the three-dimensional coordinates of surface points 555. In another embodiment, a topography of vertical wall 505 is approximated by applying a least squares regression to the three-dimensional coordinates.

From Block 350, the method may proceed to Block 355 by determining whether to carry out another iteration of slice and view processing of sample 400 (e.g., by repeating Block 315 through Block 350) or continue to Block 360 by terminating slice and view processing of sample 400 and generating a 3-D image of feature 412. To generate a 3-D image of a feature 412, it is desirable to obtain many images, depending on the size of the feature 412 or the desired detail of the 3-D image. In Block 355 the iterations of the slice and view technique are counted as processing of sample 400 progresses. In an embodiment, slice and view processing is carried out until a predetermined number of slice and view iterations have been carried out. In another embodiment, termination of slice and view iterations is initiated in response to the occurrence of a particular trigger event. In yet another embodiment, termination of slice and view processing depends on whether additional input is received by the slice and view processing system after a certain number of slice and view iterations have been carried out. In any case, if it is determined that slice and view processing of sample 400 should continue, the method 300 proceeds from Block 355 to Block 360 along the "No" path. If it is determined that the reiterative slicing process has concluded, the method 300 proceeds from Block 355 to Block 360 along the "Yes" path.

In Block 360, a 3-D representation of feature 412 is generated from data generated during slice and view processing of sample 400. In various embodiments, the 3-D image of feature 412 is constructed from a stack of modified slice images of vertical walls 505. In one such embodiment, a single slice image for each of vertical walls 505 is selected for modification. The single slice images may be selected from one of the first and second images captured by SEM 530 for each of the vertical walls 505, or other SEM images of the vertical walls 505 may be used. Each of the single slice images are modified by bending the slice image to conform to the 3-D curve fitted to the vertical surface 405 represented by the slice image. That is, each of the single slice images assumes a 3-dimensional curvature corresponding to the topography of the vertical wall 505 represented by the single slice image. Each of the modified slice images are then arranged in the stack according to the position of the vertical surface 405 represented by the slice image in sample 400 relative to the other slices. Alternatively, the slice images may be arranged in the stack and then modified. After modification and arrangement of the slice images, the 3-D image of feature 412 is formed from the modified and arranged slice images. By modeling sample 400 using the modified slice images having 3-D curvatures representative of the topography of the slice images rather than assuming each image represents a flat 2-D plane, the effects of curtaining on the resolution and/or image quality of 3-D representation may be reduced or eliminated because more accurate representations of the imaged surfaces are being used to model the 3-D image of the slice-and-viewed feature (e.g., feature 412).

The modeling of feature 412 may be carried out by commercially available software in conjunction with supplemental computer-executable instructions that, when executed, bend the slice images used by the commercially available software to generate the 3-D representation into the shapes of the fitted curves corresponding to the slice images. Alternatively, the supplemental computer-executable instructions may modify the commercially available software to accept as input slice images already bent into the shapes of the fitted curves corresponding to the slice images. Software for 3-D construction may preferably include, for example, Amira three-dimensional imaging software from Visage Imaging, Inc. San Diego, Calif., or Avizo three-dimensional visualization software from VSG, Visualization Sciences Group, Inc. Burlington, Mass.

An apparatus for performing the methods described above is shown in FIG. 3. illustrating a typical dual beam system 1010 with a vertically mounted SEM column and a focused ion beam (FIB) column mounted at an angle of approximately 52 degrees from the vertical. Such dual beam systems are commercially available, for example, from FEI Company, Hillsboro, Oreg., the assignee of the present application. While an example of suitable hardware is provided below, the invention is not limited to being implemented in any particular type of hardware.

A scanning electron microscope 1041, along with power supply and control unit 1045, is provided with the dual beam system 1010. An electron beam 1043 is emitted from a cathode 1052 by applying voltage between cathode 1052 and an anode 1054. Electron beam 1043 is focused to a fine spot by means of a condensing lens 1056 and an objective lens 1058. Electron beam 1043 is scanned two-dimensionally on the specimen by means of a deflection coil 1060. Operation of condensing lens 1056, objective lens 1058, and deflection coil 1060 is controlled by power supply and control unit 1045.

Electron beam 1043 can be focused onto substrate 1022, which is on movable X-Y stage 1025 within lower chamber 1026. When the electrons in the electron beam strike substrate 1022, secondary electrons are emitted. These secondary electrons are detected by secondary electron detector 1040 as discussed below. STEM detector 1062, located beneath the TEM sample holder 1024 and the stage 1025, can collect electrons that are transmitted through the sample mounted on the TEM sample holder as discussed above.

Dual beam system 1010 also includes focused ion beam (FIB) system 1011 which comprises an evacuated chamber having an upper neck portion 1012 within which are located an ion source 1014 and a focusing column 1016 including extractor electrodes and an electrostatic optical system. The axis of focusing column 1016 is tilted 52 degrees from the axis of the electron column. The ion column 1012 includes an ion source 1014, an extraction electrode 1015, a focusing element 1017, deflection elements 1020, and a focused ion beam 1018. Focused ion beam 1018 passes from ion source 1014 through focusing column 1016 and between electrostatic deflection means schematically indicated at 1020 toward substrate 1022, which comprises, for example, a semiconductor device positioned on movable X-Y stage 1025 within lower chamber 1026.

Stage 1025 can preferably move in a horizontal plane (X and Y axes) and vertically (Z axis). Stage 1025 can also tilt approximately sixty (60) degrees and rotate about the Z axis. In some embodiments, a separate TEM sample stage (not shown) can be used. Such a TEM sample stage will also preferably be moveable in the X, Y, and Z axes. A door 1061 is opened for inserting substrate 1022 onto X-Y stage 1025 and also for servicing an internal gas supply reservoir, if one is used. The door is interlocked so that it cannot be opened if the system is under vacuum.

An ion pump 1028 is employed for evacuating neck portion 1012. The chamber 1026 is evacuated with turbomolecular and mechanical pumping system 1030 under the control of vacuum controller 1032. The vacuum system provides within chamber 1026 a vacuum of between approximately $1 \times 10^{-7}$ Torr and $5 \times 10^{-4}$ Torr. If an etch assisting, an etch retarding gas, or a deposition precursor gas is used, the chamber background pressure may rise, typically to about $1 \times 10^{-5}$ Torr.

The high voltage power supply provides an appropriate acceleration voltage to electrodes in focusing column 1016 for energizing and focusing ion beam 1018. When it strikes substrate 1022, material is sputtered, that is physically ejected, from the sample. Alternatively, ion beam 1018 can decompose a precursor gas to deposit a material.

High voltage power supply 1034 is connected to liquid metal ion source 1014 as well as to appropriate electrodes in ion beam focusing column 1016 for forming an approximately 1 keV to 60 keV ion beam 1018 and directing the same toward a sample. Deflection controller and amplifier 1036, operated in accordance with a prescribed pattern provided by pattern generator 1038, is coupled to deflection plates 1020 whereby ion beam 1018 may be controlled manually or automatically to trace out a corresponding pattern on the upper surface of substrate 1022. In some systems the deflection plates are placed before the final lens, as is well known in the art. Beam blanking electrodes (not shown) within ion beam focusing column 1016 cause ion beam 1018 to impact onto blanking aperture (not shown) instead of substrate 1022 when a blanking controller (not shown) applies a blanking voltage to the blanking electrode.

The liquid metal ion source 1014 typically provides a metal ion beam of gallium. The source typically is capable of being focused into a sub one-tenth micrometer wide beam at substrate 1022 for either modifying the substrate 1022 by ion milling, enhanced etch, material deposition, or for the purpose of imaging the substrate 1022.

A charged particle detector 1040, such as an Everhart Thornley or multi-channel plate, used for detecting secondary ion or electron emission is connected to a video circuit 1042 that supplies drive signals to video monitor 1044 and receiving deflection signals from a system controller 1019. The location of charged particle detector 1040 within lower chamber 1026 can vary in different embodiments. For example, a charged particle detector 1040 can be coaxial with the ion beam and include a hole for allowing the ion beam to pass. In other embodiments, secondary particles can be collected through a final lens and then diverted off axis for collection.

A micromanipulator 1047, such as the AutoProbe 1000™ from Omniprobe, Inc., Dallas, Tex., or the Model MM3A from Kleindiek Nanotechnik, Reutlingen, Germany, can precisely move objects within the vacuum chamber. Micromanipulator 1047 may comprise precision electric motors 1048 positioned outside the vacuum chamber to provide X, Y, Z, and theta control of a portion 1049 positioned within the vacuum chamber. The micromanipulator 1047 can be fitted with different end effectors for manipulating small objects. In the embodiments described herein, the end effector is a thin probe 1050.

A gas delivery system 1046 extends into lower chamber 1026 for introducing and directing a gaseous vapor toward substrate 1022. U.S. Pat. No. 5,851,413 to Casella et al. for "Gas Delivery Systems for Particle Beam Processing," assigned to the assignee of the present invention, describes a suitable gas delivery system 1046. Another gas delivery system is described in U.S. Pat. No. 5,435,850 to Rasmussen for a "Gas Injection System," also assigned to the assignee of the present invention. For example, iodine can be delivered to enhance etching, or a metal organic compound can be delivered to deposit a metal.

System controller 1019 controls the operations of the various parts of dual beam system 1010. Through system controller 1019, a user can cause ion beam 1018 or electron beam 1043 to be scanned in a desired manner through commands entered into a conventional user interface (not shown). Alternatively, system controller 1019 may control dual beam system 1010 in accordance with programmed instructions stored in a memory 1021. In some embodiments, dual beam system 110 incorporates image recognition software, such as software commercially available from Cognex Corporation, Natick, Mass., to automatically identify regions of interest, and then the system can manually or automatically extract samples in accordance with the invention. For example, the system could automatically locate similar features on semiconductor wafers including multiple devices, and take samples of those features on different (or the same) devices.

It various embodiments, it may be desirable to carry out method 300 with a beam system. In some such embodiments, the beam system is a dual charged particle beam system comprising an etching beam column, configured to expose surfaces of the sample by emitting an etching beam that removes material from the sample, and an interrogating beam column, configured to image the surfaces exposed by emitting an interrogating beam.

Figure 11:
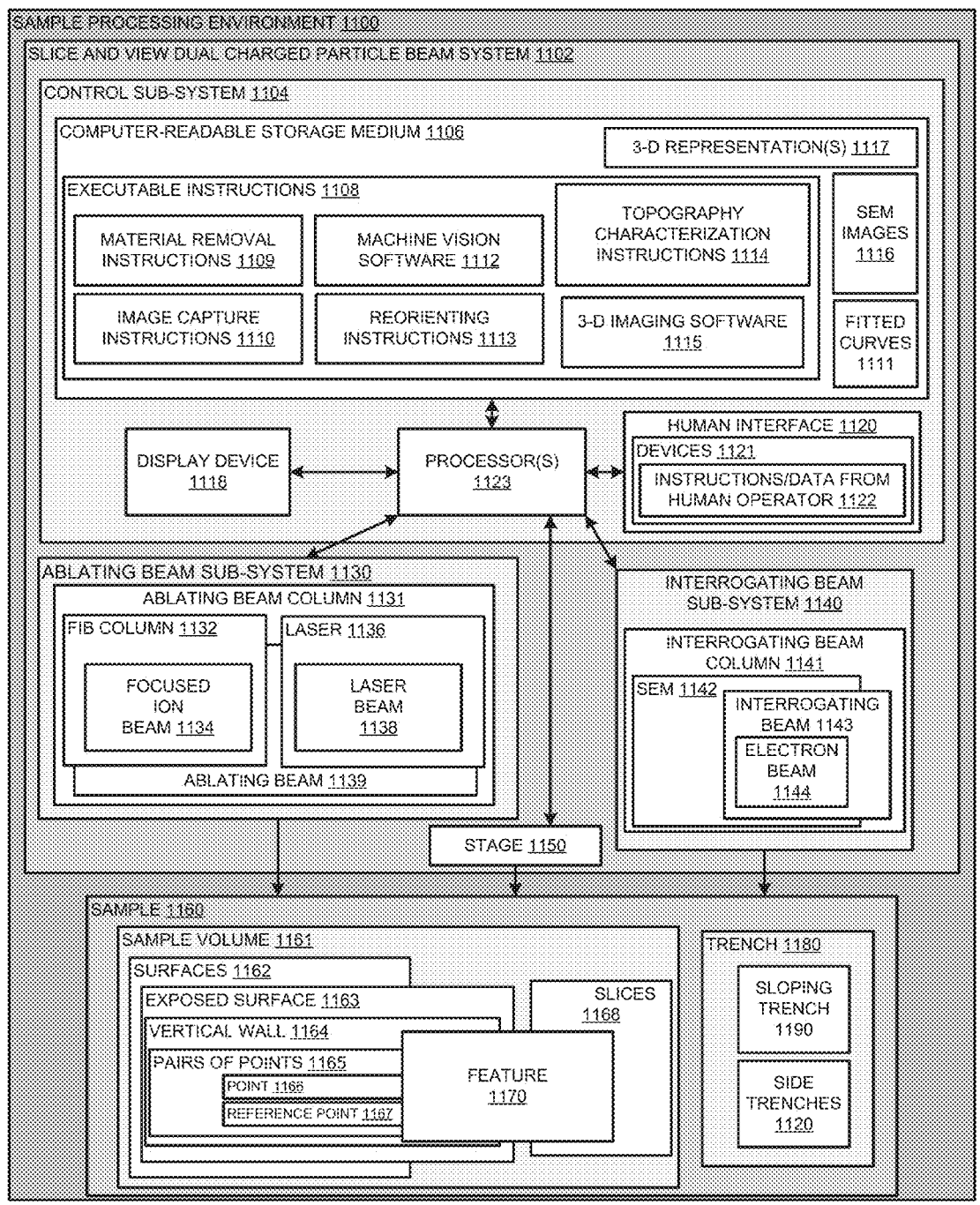
FIG. 11 is a block diagram of an embodiment of a slice and view dual charged particle beam system 1102 according to an embodiment.

Referring now to FIG. 11, a block diagram of an embodiment of a slice and view dual charged particle beam system 1102 is shown. System 1102 comprises a control sub-system 1104, an etching beam sub-system 1130, an interrogating beam sub-system 1140, and a stage 1150 configured to work in cooperation to carry out slice and view processing of a sample such as, for example, sample 1160. Sample 1160 comprises a sample volume 1161 containing all or part of a feature 1170 to be observed by removing slices 1168 of sample volume 1161 and imaging surfaces 1162 exposed by removal of slices 1168. The slices may be cut such that each of the slices 1168 is a vertical wall 1164 (i.e., normal the base plane of sample 1160 in contact with stage 1150) of a trench 1180 formed in a surface of sample 1160. By carrying out a slice and view processing of sample 1160 using system 1102, a 3-D representation (e.g., a 3-D image) of feature 1170 may be formed.

Etching beam sub-system 1130 comprises an etching beam column 1131 configured to emit an emit etching beam 1139 and to remove slices 1168 by emitting etching beam 1139. In an embodiment, etching beam column 1131 is a FIB column 1132 configured to emit a focused ion beam 1134. In another embodiment, etching beam column 1131 is a laser 1136 comprising laser beam 1138. Still other embodiments comprise multiple etching beam columns and/or types of etching beam columns. Etching beam sub-system is configured to carry out removal of material in accordance with material removal instructions 1109 stored on computer-readable storage medium 1106.

Interrogating beam sub-system 1140 comprises interrogating beam column 1141, which is configured to emit interrogating beam 1143 to capture images of surfaces 1162 of sample 1160 exposed by etching beam sub-system 1130. In an embodiment, interrogating beam column 1141 is a SEM 1142 and interrogating beam 1143 is an electron beam 1144. In another embodiment, interrogating beam column 1141 is a FIB device and interrogating beam 1143 is a focused ion beam. Embodiments of system 1102 are not limited to a single interrogating beam column, a single type of interrogating beam column, or a single type of interrogating beam. In various embodiments, interrogating beam 1141 is configured to interrogate surfaces 1162 from different angles of incidence such that images of the surfaces may be captured from different perspectives as described above.

In various embodiments, a single beam column is used in both etching beam sub-system 1130 and interrogating beam sub-system 1140. That is, some embodiments of the disclosure comprise a beam column configured to emit etching beam 1131 for removing slices 1168 from sample 1160, decorating surfaces 1162, and/or forming trench 1180 and also an interrogating beam 1141 for imaging surfaces 1162 exposed by etching beam 1131. In some embodiments, the slice and view beam system comprises a single charged particle beam column capable of removing material from a sample and imaging surfaces exposed by removing material from the sample. In one such embodiment, the single charged particle beam column is an FIB device, configured to emit both etching beams and interrogating beams. In other embodiments, the slice and view beam system comprises a dual charged particle beam system 1102 comprising an etching beam column 1131 and a separate interrogating beam column 1140, wherein the etching beam column 1131 is capable of emitting both etching beam 1139 and interrogating beam 1143. In such embodiments, the dual charged particle beam system 1102 is configured to operate in at least two of the following three modes. In the first mode, etching beam column 1131 carries out etching tasks (e.g., removing slices, decorating surfaces, forming trenches) and the interrogating tasks (e.g., capturing the first images and the second images), and interrogating beam column 1141 carries out neither etching tasks nor interrogating tasks. In the second mode, etching beam column 1131 carries out etching tasks and interrogating tasks, and interrogating beam column 1141 also carries out interrogating tasks but not etching tasks. In the third mode, etching beam column 1131 carries out etching tasks but not interrogating tasks, and interrogating beam column 1141 carries out interrogating tasks but not etching tasks. In one such dual charged particle beam system 1102, the etching beam column 1131 is a FIB device and the interrogating beam column 1141 is a SEM. The FIB device can also be used to form an image and so can function as both the etching beam and the interrogating beam. An electron beam can etch in the presence of an etch precursor gas, as well as forming an image.

Stage 1150 supports sample 1150 during slice and view processing. In various embodiments, stage 1150 is rotatable and configured to rotate in directions and to degrees allowing an surface 1163 of sample 1162 to be imaged from different angles of incidence by interrogating beam 1143. Stage 1025, as described above, is an example of a stage suitable for use in system 1102.

Control sub-system 1104 comprises a computer-readable storage medium 1106, a display device 1118, human interface 1120, and one or more processors 1123. Computer-readable storage medium 1104 stores processor accessible information comprising executable instructions 1108, 2-D images captured by interrogating beam system 1140, such as SEM images 1116 captured by SEM column 530, and 3-D representations 1117 of feature 412 generated by information (e.g., SEM images of exposed samples surfaces, 3-D coordinates of points on the exposed surfaces) obtained via slice and view processing of sample 1160. Computer-readable storage medium 1104 is coupled to one or more processors 1123 such that one or more processors 1123 can read and execute executable instructions 1108, process data acquired from at least one of sub-systems 1130 and 1140, human interface 1120, and stage 1150 in accordance with executable instructions 1108, direct the writing of data acquired from at least one of sub-systems 1130 and 1140, human interface 1120, and stage 1150 to computer-readable storage medium 1106. Computer-readable storage medium may be a device capable of storing information for a period of time in a format readable by a computer, such as a hard drive. Examples of suitable computer-readable storage mediums include, but are not limited to, PATA, SATA, SCSI, and SSD hard drives.

Display device 1118 may be configured to display information from one or more of sub-systems 1104, 1130, 1150, and stage 1150. Display device 1118 projects electronically generated images, which may include, for example, 3-D representations 1117 generated from the slice and view processing of sample 1160, SEM images 1116 captured with respect to surfaces 1162, 3-D representations of curves fitted to topographies of surfaces 1162, or any combination thereof. Examples of suitable display devices include, but are not limited to, LCD displays, plasma displays, cathode rays tube displays, and wall projectors.

Human interface 1120 comprises devices 1121 configured to enable human interaction with sub-systems 1104, 1130, 1140, and 1150. Human interaction with sub-systems 1104, 1130, 1140, and 1150 may include, for example, the inputting by a human operator of instructions and/or data 1122 for controlling slice and view processing of a sample and/or for manipulating experimental data produced therefrom. Examples of devices suitable for human interface 1120 include, but are not limited to, keyboards, computer mice, touch interfaces such as tablet computers, or any combination thereof. Human interface 1120 also comprises executable instructions for managing the interactions of human operators with system 1102.

One or more processors 1123 carry out executable instructions 1108 stored on computer-readable storage medium 1106, thereby controlling sub-systems 1131 and 1140. One or more processors 1123 also read and send information to display device 1118 for viewing by a human operator and/or observer. For example, in various embodiments one or more processors 1123 access 3-D representations 1117 and/or SEM images 1116 stored on computer-readable storage medium 1106. In such embodiments, one or more processors 1123 also direct display device 1118 to display 3-D representations 1117 and/or SEM images 11116. One or more processors 1123 further process instructions and/or data 1122 in accordance with executable instructions 1108 and direct the storage of data acquired from sub-systems 1130 and 1140, human interface 1120, and stage 1150 on computer-readable storage medium 1106.

Embodiments of slice and view processing of the disclosure, such as method 300 described above, may be carried out by system 1102 according to executable instructions 1108 stored on computer-readable storage medium 1106 of system 1102. Executable instructions 1108 comprise material removal instructions 1109, machine vision software 1110, image capture instructions 1112, reorienting instructions 1113, topography characterization instructions 1114, and 3-D imaging software 1115.

Material removal instructions 1109 include instructions for removing slices 1168 to expose surfaces 1162. Material removal instructions 1109, when executed, cause one or more processors 1123 to direct etching beam 1139 to remove slices 1168 in sequential order across a thickness of sample volume 1161, the removal of each slice 1169 exposing a surface 1163 of surfaces 1162.

In various embodiments, material removal instructions 1109 include additional instructions that, when executed, cause the one or more processors 1123 to direct etching beam 1139 to carry out one or more other material removal tasks. The other material removal tasks include, but are not limited to, milling sloping trench 1190 such that interrogating beam 1144 can interrogate an exposed surface 1163 without being obstructed by other portions of sample 1160; milling a fiducial near sample 1160 to facilitate accurate positioning of etching beam 1139; milling side trenches 1120 such that interrogating beam 1144 can capture second images of surfaces 1162 at greater degrees of stage rotation and/or beam repositioning (e.g., steps 335 and 340 of method 300, supra) without being obstructed by other portions of sample 1160; milling machine-identifiable shapes on surfaces 1162 (e.g., steps 335 and 340 of method 300, supra); and any combination thereof.

For each exposed surface 1163, the one or more processors 1123 direct components of system 1102 to carry out one or more image capture instructions 1110. Image capture instructions 1110, when executed, cause one or more processors 1123 to direct interrogating beam 1143 to interrogate an exposed surface 1163 while substantially maintaining a first angle of incidence between a longitudinal axis of the interrogating beam column 1141 and exposed surface 1163, thereby capturing a first image of exposed surface 1163. Image capture instructions 1110, when executed, cause one or more processors 1123 to direct interrogating beam 1143 to interrogate exposed surface 1163 while substantially maintaining a second angle of incidence between a longitudinal axis of the interrogating beam column 1141 and exposed surface 1163, thereby capturing a second image of exposed surface 1163. The image information recorded by interrogating beam 1142 is processed by the one or more processors 1123 using machine vision software 1112, and one or more processors 1123 may direct the captured images to be stored in the machine-readable storage medium 1106. Additional information, including examples of machine vision software suitable for embodiments of system 1102 is described in more detail above.

The changing of the first angle of incidence to the second angle of incidence is carried out by executing reorienting instructions 1113. Reorienting instructions 1113 include instructions for changing the angle of incidence of interrogating beam 1143 on exposed surface 1163 after the first image of exposed surface 1163 has been captured by interrogating beam 1143. Additionally or alternatively, reorienting instructions 1113 include instructions for changing the angle of incidence of interrogating beam 1143 on exposed surface 1163 by directing a translation of interrogating beam column 1141 away from a longitudinal axis of interrogating beam column during interrogation of exposed surface 1163 at the first angle of incidence. The degree of reorientation should be such that values of distances between pairs of points 1165 measured in the second image of exposed surface 1163 are different than values of distances measured between the same pairs of points 1165 in the first image of exposed surface 1163. Executable instructions 1108, when executed, cause one or more processors 1123 to carry out the image capture instructions 1110 for capturing the second image after an execution of reorienting instructions reorientation 1113 has taken place and before a removal of a slice 1168.

Topography characterization instructions 1114 include instructions that, when executed, cause the one or more processors 1123 to generate curves 1111 fitted to topographies of surfaces 1162. Topography characterization instructions 1114 include instructions to record first positions of pairs of points 1165 in the first image and second positions of pairs of points 1165 in the second image, wherein each pair of points 1165 comprises a reference point 1167 and a point 1166 on exposed surface 1163.

For each pair of points 1165, reference point 1167 refers to a fixed position relative to point 1166 on exposed surface 1163. The reference point 1167 of pairs of points 1165 may be the same reference point (e.g., points $B_1$-$B_6$ in FIGS. 8A-8B and 9B-9C all refer to a common reference point A), a different reference point may be used for each pair of points 1165, or some of pairs of points 1165 may share common reference points while the reference points of other pairs of points 1165 are unique. Positions for the reference points 1167 may be any location on or above the sample visible in both the first image and the second image of the exposed surface 1163 being imaged. In various embodiments, both the reference points 1167 and pairs of points 1165 are located on the exposed surface 1163. In one such embodiment, a reference point 1167 is selected for each of pairs of points 1165 at a position on exposed surface 1163 near or overlapping a corner of exposed surface 1163.

The quantity of pairs of points 1165 and the position of at least one of reference point 1167 and point 1166 for each of the pair of points 1165 may be generated, randomly or otherwise, according to topography characterization instructions 1114 executed by one or more processors 1123, input via human interface 1120 by a human operator, or a combination thereof. The quantity of pairs of points 1165 and the position of at least one of reference point 1167 and point 1166 for each of the pair of points 1165 may be selected to facilitate the generation of more precise fitted curves 1111, selected to satisfy a desired balance between speed of sample processing and precision the fitted curves 1111 generated, or any combination thereof.

In various embodiments, the system 1102 utilizes machine vision software 1112 to ascertain the positions of reference points 1167 and points 1166. Machine vision software 1112 may determine positions of the reference points 1167 and points 1166 immediately by immediately processing the image information as it is obtained by interrogating beam 1143, or processing may occur at a later time, such as after the imaging of the last surface 1162.

In various embodiments, the execution of topography characterization instructions 1114 may be facilitated by milling machine-identifiable shapes on the exposed surface 1163 at positions corresponding to points of pairs of points 1165. In such embodiments, the material removal instructions 1109 comprise instructions for milling machine-identifiable shapes on one or more of surfaces 1162 at positions corresponding to reference points 1167, points 1166, or both the reference points 1167 and points 1166 of pairs of points 1165. The presence of machine-identifiable shapes on surfaces 1162 improves the ability of machine vision software 1112 to track the position of the reference points 1167 and points 1166 on an exposed surface 1163 from the first image to the second image (i.e., find the same positions on the surface exposed in both images). The machine-identifiable shapes may comprise one or more substantially 2-dimensional shapes identifiable by pattern recognition algorithms of machine vision software 1112. Examples of suitable machine-identifiable shape shapes include, but are not limited to basic geometric shape, such as circles, squares, triangles, and rectangles, and simple symbols, such as the symbols shown in FIGS. 6A-6B, 8A-8B, and 9B-9C. In various embodiments, material removal instructions 1109 comprises instructions for providing surfaces 1162 with differently-shaped machine-identifiable shapes. Varying the shape of machine-identifiable shapes used for points on an exposed surface 1163 reduces or eliminates the likelihood that points shown in the first image of the exposed surface 1163 will be mistaken for different points having the same or a similar shape of machine-identifiable shape in the second image of the exposed surface 1163. The likelihood of misidentification of misidentifying points on exposed surface 1163 decreases as the diversity of machine-identifiable shape shapes employed increases. In an embodiment, the machine-identifiable shapes used to identify points on an exposed surface 1163 comprise at least two shapes. In another embodiment, a different machine-identifiable shape is used to mark each of points 1166 on an exposed surface 1163.

Topography characterization instructions 1114 include instructions to determine elevations for each of points 1166 using the following Formula (2):

$$Z = \frac{|\overline{A'B'}| - |\overline{AB}|\cos\theta}{\sin\theta}, \quad \text{Formula (2)}$$

wherein Z is the elevation of the point 1166, A is a position of the reference point 1167 in the first image, A' is a position of the reference point 1167 in the second image, B is a position of point 1166 on exposed surface 1163 in the first image, B' is a position of the point 1166 on exposed surface 1163 in the second image, $|\overline{A'B'}|$ is the distance between A' an B', $|\overline{AB}|$ is the distance between A and B, and θ is the difference between the first angle of incidence and the second angle of incidence.

Topography characterization instructions 1114 further include instructions to generate 3-D coordinates for each of points 1166. In an embodiment, the coordinates of each point 1166 comprises the x and y coordinates of the point 1166 on the imaging plane (see FIG. 1), as measured from an arbitrary origin, and the elevation of the point 1166, as determined by Formula (1). Topography characterization instructions 1114 further comprises executable algorithms for fitting 3-D curves to the 3-D coordinates. Examples of algorithms suitable for fitting 3-D curves to the 3-D coordinates include, but are not limited to, least squares regression and Fourier Transform analysis.

System 1102 utilizes 3-D imaging software 1115 to generate 3-D representations of features 1170 processed by system 1102. The executable instructions 1108 of system 1102 may comprise instructions for generating 3-D representations of feature 1170 after slice and view processing feature 1170 according to executable instructions 1108 using system 1102. 3-D imaging software 1115 may include executable instructions that, when executed, use the 3-D fitted curves 1111 to eliminate or reduce the effect of curtaining on the resolution and/or image quality of 3-D representation 1117. In an embodiment, system 1102 comprises 3-D imaging software 1115 that, when executed by one or more processors 1123, generates 3-D representations of a feature 1170 processed according to slice and view processing using images of surfaces 1163 and assuming that surfaces 1163 are flat. System 1102 further comprises supplemental executable instructions that, when executed by one or more processors 1123, modify execution of 3-D imaging software 1115 by bending the images of surfaces 1163 to correspond to fitted curves 1111, and then using the bent images of surfaces 1163 (instead of the flat images of surfaces 1163) to generate the 3-D representation of feature 1170.

In various embodiments, system 1102 is configured to carry out the steps of method 300. In some embodiments, system 1102 is configured to coordinate the execution of executable instructions 1109, 1110, 1112, 1113, 1114, and 1115 (e.g., via a set of executable coordinating instructions). In one such embodiment, system 1102 is configured to carry out image capture instructions 1110 before and after reorienting instructions 1113 for each surface 1163 exposed by removal of a slice 1168. In said embodiment, system 1102 is also configured to execute topography characterization instructions 1114 on the sets of 3-D coordinates generated for one or more of surface 1162. In embodiments utilizing machine-identifiable shapes, system 1102 is configured to execute material removal instructions for decorating surfaces 1162 after exposure of each exposed surface 1163 and before the first execution of image capture instructions 1110 for the same exposed surface 1163. System 1102 may be configured to carry out executable instructions 1108 automatically, semi-automatically, by instructions manually entered into human interface 1120 by a human operator, or any combination thereof. System 1102 may be configured to determine the appropriate number of surfaces to be sliced and viewed given one or more parameters (e.g., desired resolution, time available to complete processing, sample characteristics, etc.), which may be stored on computer-readable storage medium 1106, input by a human operator via human interface 1120, or a combination thereof. System 1102 may be configured to iteratively slice and view the sample 1160 a number of times determined by system 1102 to be appropriate for a given set of parameters, each slice and view iteration carried out via execution of executable instructions 1109, 1110, 1112, 1113, 1114, and 1115. It should be understood that executable instructions 1109-1115 are illustrated in FIG. 11 as discrete blocks to facilitate understanding of various embodiments of the disclosure, and do not imply limitations of functionality for system 1102.

System 1102 may be utilized in sample processing environment 1100. Examples of sample processing environment 1100 include, but are not limited to, laboratories and other experimental facilities for carrying out analysis of biological samples, failure analysis of mechanical components, quality control in material manufacture, and defect testing of electronic components such as silicon wafers and other semiconductor components.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible, and alternative embodiments that result from combining, integrating, and/or omitting features of the embodiments disclosed herein are also within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_1$ and an upper limit, $R_u$, is disclosed, any number falling within the range is specifically disclosed. In particular, the following numbers within the range are specifically disclosed: $R=R_1+k*(R_u-R_1)$, wherein k is a variable ranging from 1 percent to 100 percent with a 1 percent increment, i.e., k is 1 percent, 2 percent, 3 percent, 4 percent, 5 percent, 50 percent, 51 percent, 52 percent, 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as "comprises," "includes," "having," etc. should be understood to provide support for narrower terms such as "consisting of," "consisting essentially of," "comprised substantially of," etc.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The discussion of a reference in the Detailed Description of the Embodiments is not an admission that it is prior art to the present invention, especially any reference that may have a publication date after the priority date of this application.

I claim as follows:

1. An apparatus for observing a feature using dual charged particle beams, comprising: a focused ion beam column configured to generate, focus, and direct a focused ion beam;
   an electron beam column configured to generate, focus, and direct an electron beam;
   one or more processors; and
   a computer-readable storage medium coupled to at least one of the one or more processors, the computer-readable storage medium comprising first executable instructions and second executable instructions,
   wherein the first executable instructions, when executed, cause the one or more processors to direct the focused ion beam to mill a trench in a surface of a substrate, the trench exposing a vertical wall having an area around a feature to be observed, and
   wherein the second executable instructions, when executed, cause the one or more processors to:
      direct the electron beam to capture a first electron beam image of the vertical wall while the electron beam column is maintained at a first angle of incidence relative to a longitudinal axis of the electron beam column;
      change the angle of incidence between the longitudinal axis and the vertical wall from the first angle of incidence to a second angle of incidence;
      direct the electron beam to capture a second electron beam image of the wall while the electron beam column is maintained at the second angle of incidence; and
      approximate a topography of the vertical wall based on differences between the first electron beam image and the second electron beam image.

2. The apparatus of claim 1, wherein approximation of the topography of the vertical wall comprises calculating three-dimensional coordinates for a plurality of points on the vertical wall using positions of the plurality of points in the first electron beam image and the second electron beam image relative to a reference point in the first electron beam image and the second electron beam image.

3. The apparatus of claim 2, wherein approximation of the topography of the vertical wall comprises fitting a curve to the three-dimensional coordinates that approximates the topography of the vertical wall.

4. The apparatus of claim 1, wherein approximation of the topography of the vertical wall based on differences between the first electron beam image and the second electron beam image comprises:
   measuring in the first electron beam image first distances between a plurality of points on the vertical wall and one or more reference points on the vertical wall; and
   measuring in the second electron beam image second distances between the plurality of points and the one or more reference points.

5. The apparatus of claim 1, wherein the second executable instructions, when executed, cause the one or more processors to change the angle of incidence of between the longitudinal axis and the vertical wall by directing a rotation of a stage.

6. The apparatus of claim 1, wherein the second executable instructions, when executed, cause the one or more processors to change the angle of incidence of between the longitudinal axis and the vertical wall by directing a repositioning of the electron beam column.

7. The apparatus of claim 1, further comprising third executable instructions that, when executed, cause the one or more processors to:

direct the focused ion beam to sequentially remove a plurality of slices from a volume of material located behind the vertical wall, wherein the volume of material comprises a feature to be observed and sequentially removing the plurality of slices sequentially exposes a plurality of additional vertical walls; and carry out the second executable instructions for each vertical wall of the plurality of additional vertical walls.

8. The apparatus of claim 7, further comprising fourth executable instructions that, when executed, cause the one or more processors to construct a three-dimensional image of the feature to be observed using the approximations of the topographies of the vertical wall and the plurality of additional vertical walls.

9. A method of processing a sample by slice and view processing with a dual beam system, comprising:

exposing a vertical wall of a trench formed in a surface of a sample by removing a first slice of material from the sample using an etching beam;

capturing a first image of the vertical wall by interrogating the vertical wall with an interrogating beam while the vertical wall is at a first orientation relative to the interrogating beam;

reorienting the vertical wall relative to the interrogating beam;

capturing a second image of the vertical wall by interrogating the vertical wall with the interrogating beam while the vertical wall is at a second orientation relative to the interrogating beam, wherein first distances in the first image between a reference point and surface points on the vertical wall are different than second distances in the second image between the reference point and the surface points;

determining elevations of the surface points using the first distances and the second distances; and fitting a curve to a topography of the vertical wall using the elevations.

10. The method of claim 9, wherein fitting the curve to the topography of the vertical wall comprises generating three-dimensional coordinates for the surface points, wherein the three-dimensional coordinates comprise a vertical location, a horizontal location, and an elevation for each of the surface points.

11. The method of claim 10, wherein fitting the curve to the topography of the vertical wall comprises applying a three-dimensional Fourier fit to the three-dimensional coordinates.

12. The method of claim 10, wherein fitting the curve to the topography of the vertical wall comprises applying a least squares regression to the three-dimensional coordinates.

13. The method of claim 9, wherein the vertical wall is a first vertical wall and further comprising:

exposing a subsequent vertical wall behind the first vertical wall by applying the etching beam to the first vertical wall such that a subsequent slice of material is removed from a surface of the first vertical wall; and applying the steps of capturing a first image, reorienting, capturing a second image, determining elevations, and fitting a curve to the subsequent vertical wall.

14. The method of claim 13, further comprising:

carrying out the steps of claim 13 a number of times in connection with a series of successively exposed vertical walls to produce a number of fitted curves representing the series of successively exposed vertical walls; and generating a three-dimensional representation of a feature of the sample using the number of fitted curves.

15. The method of claim 9, wherein reorienting the vertical wall relative to the interrogating beam comprises changing an angle of incidence between the interrogating beam and the vertical wall by translating a source of the interrogating beam away from a longitudinal axis of the interrogating beam during the capturing the first image.

16. The method of claim 9, wherein reorienting the vertical wall relative to the interrogating beam comprises rotating the sample.

17. The method of claim 16, wherein the elevations are determined according to the following formula:

$$Z_i = \frac{|\overline{A_i' B_i'}| - |\overline{A_i B_i}|\cos\theta}{\sin\theta},$$

wherein $Z_i$ is the elevation of a point i of the surface points, $A_i$ is a position of the reference point in the first image, $A_i'$ is a position the reference point in the second image, $B_i$ is a position of point i in the first image, $B_i'$ is a position of point i in the second image, $|\overline{A_i' B_i'}|$ is the distance between $A_i'$ and $B_i'$ $|\overline{A_i B_i}|$ is the distance between $A_i$ and $B_i$, and $\theta$ is the difference of a first angle of incidence and a second angle of incidence.

18. A particle beam system for slice and view processing a volume of a sample having a feature to be observed, comprising:

an etching beam column configured to emit an etching beam;

an interrogating beam column configured to emit an interrogating beam;

one or more processors; and a computer-readable storage medium coupled to at least one of the one or more processors, the computer-readable storage medium comprising executable instructions that, when executed, cause the one or more processors to direct the etching beam to sequentially remove slices of the sample across a thickness of the volume, the removal of each slice exposing a surface of the sample, and, for each surface exposed:

direct the interrogating beam to capture a first image of the surface exposed while maintaining a first angle of incidence between a longitudinal axis of the interrogating beam column and the surface exposed and a second image of the surface exposed while maintaining a second angle of incidence between the longitudinal axis and the surface exposed, and record first positions of pairs of points in the first image and second positions of the pairs of points in the second image, wherein each of the pairs of points comprises a point on the surface exposed and a reference point.

19. The particle beam system of claim 18, wherein the executable instructions, when executed, direct the one or more processors to determine an elevation for the point on the surface exposed of each of the pairs of points according to the following formula:

$$Z = \frac{|\overline{A'B'}| - |\overline{AB}|\cos\theta}{\sin\theta},$$

wherein Z is the elevation of the point on the surface exposed, A is a position of the reference point in the first image, A' is a position of the reference point in the second image, B is a position of point on the surface exposed in the first image, B' is a position of the point on the surface exposed in the second image, $|\overline{A'B'}|$ is the distance between A' an B', $|\overline{AB}|$ is the distance between A and B, and θ is the difference between the first angle of incidence and the second angle of incidence.

20. The particle beam system of claim 18, wherein the reference point of each of the pairs of points is a same reference point.

21. The particle beam system of claim 18, wherein the executable instructions, when executed, cause the one or more processors to direct the etching beam to mill machine-identifiable shapes on the surface exposed, wherein the machine-identifiable shapes correspond to the points on the surface exposed.

22. The particle beam system of claim 21, wherein the machine-identifiable shapes comprise two or more different shapes.

23. The particle beam system of claim 18, wherein the interrogating beam comprises an electron beam and the etching beam comprises a charged particle beam.

24. The particle beam system of claim 18, wherein each surface exposed is a vertical wall of a trench formed in a surface of the sample.

25. The particle beam system of claim 18, wherein the etching beam column and the interrogating beam column are the same.

\* \* \* \* \*